US006664230B1

(12) United States Patent
Fogelman et al.

(10) Patent No.: US 6,664,230 B1
(45) Date of Patent: Dec. 16, 2003

(54) ORALLY ADMINISTERED PEPTIDES TO AMELIORATE ATHEROSCLEROSIS

(75) Inventors: Alan M. Fogelman, Beverly Hills, CA (US); Gattadahalli M. Anantharamaiah, Birmingham, AL (US); Mohamad Navab, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/645,454

(22) Filed: Aug. 24, 2000

(51) Int. Cl.$^7$ ............... A61K 38/08; A61K 38/10; A61K 38/16; C07K 7/06; C07K 7/08
(52) U.S. Cl. ............... 514/13; 514/12; 514/14; 514/15; 530/324; 530/325; 530/326; 530/327; 530/328; 530/345
(58) Field of Search ............... 514/12, 13, 14, 514/15, 21; 530/324, 325, 326, 327, 328, 375

(56) References Cited

U.S. PATENT DOCUMENTS

| | | | |
|---|---|---|---|
| 3,767,040 A | 10/1973 | Tushaus | 428/352 |
| 4,155,913 A | 5/1979 | Hellerbach et al. | 546/276 |
| 4,643,988 A | 2/1987 | Segrest et al. | 514/12 |
| 5,721,138 A | 2/1998 | Lawn | 435/325 |
| 5,733,549 A | 3/1998 | Yamada et al. | 424/185.1 |
| 5,814,467 A | 9/1998 | Curtiss et al. | 435/7.9 |
| 5,854,238 A | 12/1998 | Kempen | 514/220 |
| 6,037,323 A | 3/2000 | Dasseux et al. | 514/12 |
| 6,086,918 A | 7/2000 | Stern et al. | 424/474 |

FOREIGN PATENT DOCUMENTS

| WO | WO 97/36927 A1 | 10/1997 |
|---|---|---|
| WO | WO 99/47566 A1 | 9/1999 |

OTHER PUBLICATIONS

Pharmalicensing (Jan. 27, 2001) Esperion Builds a Novel Peptides Program (2 pages).
Pharmalicensing (Jan. 28, 2001) Unigene to Receive Patent for Delivery of Peptide Pharmaceuticals (2 pages).
Purdue News (Oct. 2000) 'Microspheres' Offer Promise for Oral Drug Delivery (3 pages).
Purdue News (Sep. 12, 1997) New Oral Insulin Delivery System Shows Promise (3 pages).
Pharmalicensing (Jan. 28, 2001) Multiple Peptide Systems Forms Joint Venture With Elan.
The Wall Street Journal (Jan. 13, 2000) Emisphere technologies develops oral Heparin.
Lancet (Sep. 25, 1999) New options developed for needle–free drug delivery.
Navab et al. (2000) Normal high density lipoprotein inhibits three steps in the formation of mildly oxidized low density lipoprotein: Step 1, *J. Lipid Res.*, 41: 1481–1494.
Navab et al. (2000) Normal high density lipoprotein inhibits three steps in the formation of mildly oxidized low density lipoprotein: Steps 2 and 3, *J. Lipid Res.*, 41: 1495–1508.
Su and Amidon (1995) Investigation into the intestinal metabolism of [D–Ala] peptide T amide: implication for oral drug delivery, *Biochim et Biophys.*, 1245: 62–68.
Garber et al. (1992) Turnover of Synthetic Class A Amphipathic Peptide Analogues of Exchangeable Apolipoproteins in Rats, *Arteriosclerosis and Thrombosis*, 12(8): 886–894.
Nagata et al. (1994) Distribution of free D–serine in vertebrate brains, *Brain Res.*, 634: 291–295.

(List continued on next page.)

*Primary Examiner*—Jeffrey E. Russel
(74) *Attorney, Agent, or Firm*—Quine Intellectual Property Law Group, PC; Tom Hunter

(57) ABSTRACT

This invention provides novel peptides that ameliorate one or more symptoms of atherosclerosis. The peptides are highly stable and readily administered via an oral route.

61 Claims, 13 Drawing Sheets

Feeding Mice ApoA-I Mimetic D-Peptides Renders Circulating LDL Resistant to Oxidation

OTHER PUBLICATIONS

Nagata et al. (1995) Free D–serine concentration in normal and Alzheimer human brain, *Brain Res. Bull.*, 38(2): 181–183.

Armstrong et al. (1993) D amino acid levels in human physiological fluids, *Chirality*, 5: 375–378.

Ohtani et al. (1995) Age–related changes in D–aspartic acid of rat teeth, *Growth Develop. & Aging*, 59: 55–61.

Pilone (2000) D–amino acid oxidase: new findings. *CMLS, Cell. Mol. Life Sci.*, 57: 1732–1747.

Tsai et al. (1998) D–serine added to antipsychotics for the treatment of schizophrenia. *Biol. Psychiatry*, 44: 1081–1089.

Mor et al. (1992) Enter a new post–translational modification: D–amino acids in gene–encoded peptides, *TIBS*, 17: 481–485.

Anantharamaiah GM., "Synthetic Peptide Analogs of Apolipoproteins". *Methods in Enzymology*, (1986), 128:627–647.

Badimon et al., "Regression of Atherosclerotic Lesions by High Density Lipoprotein Plasma Fraction in the Cholesterol–fed Rabbit". *J. Clinical Investigation*, (1990), 85:1234–1241.

Garber et al., (1997), *Circulation*, 96–I–490, Abstract No. 2744.

Navab et al., "Normal High Density Lipoprotein Inhibits Three Steps in the Formation of Midly Oxidized Low Density Lipoprotein: Steps 2 and 3". *J. Lipid Res.*, (2000), 41:1495–1508.

Navab et al., "Normal High Density Lipoprotein Inhibits Three Steps in the Formation of Mildly Oxidized Low Density Lipoprotein: Steps 1". *J. Lipid Res.*, (2000), 41:1481–1494.

Anantharamaiah et al., "Studies of Synthetic Peptide Analogs of the Amphipathic Helix". *The Journal of Biological Chemistry*, (1985), 260:10248–10255.

Garber et al., "Turnover of Synthetic Class A Amphipathic Peptide Analogues of Exchangeable Apolipoproteins in Rats". *Arteriosclerosis and Thrombosis*, (1992), 12:886–894.

Gong et al., "Structural and Functional Properties of Human and Mouse Apolipoprotein A–I". *Biochimica et Biophysica Acta*, 1994, 1213:335–342.

Chris Patszty et al., "Apolipoprotein AI Transgene Corrects Apolipoprotein E Deficiency–induced Atherosclerosis in Mice". *J. Clinical Investigation*, (1994), 94:899–903.

Andrew S. Plump et al., "Human Apolipoprotein A–I Gene Expression Increases High Density Lipoprotein and Suppresses Atherosclerosis in the Apolipoprotein E–deficient Mouse". *Proceeding of the National Academy of Sciences*, (1994), 91:9607–9611.

Rubin et al., "Inhibition of Early Atherogenesis in Transgenic Mice by Human Apolipoprotein A–I". *Nature*, (1991), 353:265–267.

Prediman K. Shah et al., "Effects of Recombinant Apolipoprotein A–I$_{Milano}$ on Aortic Atherosclerosis in Apolipoprotein E–Deficient Mice". *Circulation*, (1998), 97:780–785.

Y.V. Venkatachalapathi et al., "Effect of End Group Blockage on the Properties of a Class a Amphipathic Helical Peptide". *Proteins: Structure, Function, and Genetics*, (1993), 15:349–359.

Wilson et al., "High Density Lipoprotein Cholesterol and Mortality". *Arteriosclerosis*, (1988), 8:737–741.

Anantharamaiah and Garber (1996) "Chromatographic Methods for Quantitation of Apolipoprotein A–I." *Meth. Enzymol.* 263: 267–282.

Anantharamaiah et al. (1990) "Use of Synthetic Peptide Analogues to Localize Lecithin: Cholseterol Acyltransferase Activating Domain in Apolipoprotein A–I." *Arteriosclerosis* 10: 95–105.

Anantharamaiah et al. (1993) "An Atlas of the Amphipathic Helical Domains of Human Exchangeable Plasma Apolipoproteins." Chapter 6: pp. 109–142 In: *The Amphipathic Helix* (Epand, R. M., ed), CRC Press, Boca Raton, FL.

Boffelli et al. (1997) "The uptake of cholesterol at the small–intestinal brush border membrane is inhibited by apolipoproteins." *FEBS Letters*, 411: 7–11.

Borhani et al. (1999) "Crystal structure of truncated human apolipoprotein A–I suggests a lipid–bound conformation." *Proc. Natl. Acad. Sci. USA*. 94:12291–12296.

Brouillette and Anantharamaiah (1995) "Structural models of human apolipoprotein A–I." *Biochim. Biophys. Acta* 1256: 103–129.

Chung et al. (1985) "Studies of Synthetic Peptide Analogs of the Amphipathic Helix." *J. Biol. Chem.* 60(18): 10256–10262.

Davidson et al. (1994) "The Influence of Apolipoprotein Structure on the Efflux of Cellular Free Cholesterol to High Density Lipoprotein." *J. Biol. Chem.* 269(37): 22975–22982.

Dunlop and Neidle (1997) "The Orgion and Turnover of D–Serine in Brain." *Biochemical and Biophysical Research Communication* 235:26–30.

Ehara et al. (2001) "Elevated Levels of Oxidized Low Density Lipoprotein Show a Positive Relationship With the Severity of Acute Coronary Syndromes." *Circulation* 103:1955–1960.

Epand et al. (1987) "Studies Synthetic Peptide Analog of the Amphipathic Helix" *J. Biol. Chem.* 262(19): 9389–9396.

Field et al. (2001) "Gene expression of sterol regulatory element–binding proteins in hamster small intestine." *Journal of Lipid Research* 42:1–9.

Fielding and Fielding (1995) "Molecular physiology of reverse cholesterol transport." *J. Lipid Res.* 36: 211–228.

Fielding et al. (1972) "A Protein of Lecithin: Cholester Acyltransferase." *Biochem. Biophys. Res. Comm.* 46(2):1493–1498.

Garber et al. (1999) "Protection against Atherosclerosis in Mice by a Synthetic Class A Amphipathic Peptide Analog of Apolipoprotein A–1." *Circulation* 100: 2838.

Garber et al. (2001) "A new synthetic class A amphipathic peptide analogue protects mice from diet–induced atherosclerosis." *Journal of Lipid Research* 42:–545–552.

Glomset (1968) "The Plasma lecithin: cholesterol acytransferase reaction." *J. Lipid Res.* 9:155–167.

Hashimoto et al. (2000) "Improvement of intestinal absorption of peptides: absorption of B1–Phe monoglucosylated insulin to rat intestinal brush–border membrane vesicles." *J. Pharmaceutics & Therapeutics* 50(2):197–204.

Hayry et al. "Stabile D–peptide analog of insulin–like growth factor–1 inhibits smooth muscle cell proliferation after carotid ballooning injury in the rat." *FASEB J.* 9(13):1336–1344 (1995).

Johnson et al. (1991) "Cholesterol transport between cells and high–density lipoproteins." *Biochim. Biophys. Acta.* 1085: 273–298.

Jonas (1991) "Lecithin–cholesterol acyltransferase in the metabolism of high–density lipoproteins." *Biochim. Biophys. Acta* 1084: 205–220.

Jonas (2000) Lecithin cholesterol acyltransferase. *Biochim. Biophys. Acta* 1529: 245–256.

Kigasawa et al. (1995) "Inhibition of corneal ulceration by tetrapeptidyl hydroxamic acid." *Jap. J. Ophthamology* 39(1):35–42.

Kreiger (1999) "Charting The Fate of the "Good Cholesterol": Identification and Characterization of the High–Density Lipoprotein Receptor Sr–Bi." *Ann Rev. Biochem.* 68:523–558.

Levi et al. (2000) "A retro–inverso minantibody with anti–HIV activity." *Aids Res. & Human Retruvirus* 16(1):59–65.

Man et al. (1987) D–aspartate in human brain. *J Neurochem* 48:510–515.

Mishra et al. (1995) "Effect of the Arrangement of Tandem Repeating Units of Class A Amphipathic α–Helixes on Lipid Interaction." *J. Biol. Chem.* 270: 1602–1611.

Mishra et al. (1994) "Interaction of Synthetic Peptide Analogs of the Class A" *J. Biol. Chem.* 269: 7185–7191.

Mishra et al. (1998) Studies of Synthetic Peptides of Human Apolipoprotein A–I Containing Tandem Amphipathic α–Helixes *Biochemistry* 37: 10313–10324.

Nomoto et al. (1998) "Improved of intestinal absorbtion of peptide drugs by Gyycosylation: Transport of Tetrapeptide by the Sodium Ion–Dependent D–Glucose Transporter." *J. Pharmaceutics Science* 87(3):326–332.

Oram and Yokoyama (1996) "Apolipoprotein–mediated removal of cellular cholesterol and phospholipids." *J. Lipid Res.* 37: 2473–2491.

Paigen et al. (1990) "Atherosclerosis Susceptibility Differences among Progenitors of Recombinant Inbred Strains of Mice." *Arteriosclerosis* 10: 316–323.

Palgunachari et al. (1996) "Only the Two End Xelises of Eight Tandem Amphipathic Helical Domaine of Human Apo A–I Have Significant Lipid Affinity." *Arteriosclerosis, Thrombosis, & Vascular Biology* 16: 328–338.

Pappenheimer et al. (1997) "Absorption and Excretion of Undegradable Peptides: Rols of Lipid Solubility and Net Charge." *J. Pharmacology & Experimental Therapeutics* 280(1):292–300.

Philips et al. (1993) "Plasma Lipoproteins and Progression of Coronary Artery Disease Evaluated by Angiography and Clinical Events." *Circulation* 88: 2762–2770.

Reubsaet et al. (1999) "Qualitative and quantitative aspects of the degradation of several tripeptides derived from the antitumour peptide antagonist [Arg$^6$,D–Trp$^{7,9}$,MePhe$^8$] substance P{6–11}." *J. Pharmaceut. & Biomed Analysis* 19(3–4):277–284.

Segrest et al. (1990) "Amphipathic Helc Motif: Classes and Properties." *Proteins* 8: 103–117.

Segrest et al. (1994) "The Amphipathic α Helix: A Multifunctional Structural Motif in Plasma Apolipoproteins." *Adv. Prot. Chem.* 45: 303–369.

Segrest et al. (2000) "Structure and function of apolipoprotein A–I and high–density lipoprotein." *Current Opin. Lipidol.* 11:105–115.

Segrest et al. (1974) "A Molecular Theory of Lipid–Protein Interaction in the Plasma Lipoproteins." *FEBS Lett.* 38: 247–253.

Sprecher et al. (1993) "The Low HDL Cholesterol/High Triglyceride Trait." *Arterioscler. Thromb.* 13: 495–504.

Tsimikas et al. (2001) "Measuring Circulating Oxidized Low–Density Lipoprotein to Evaluate Coronary Risk." *Circulation* 103:1930–1932.

Yancey et al. (1995) "Efflux of Cellular Cholesterol and Phospholipid to Lipid–free Apolipoproteins and Class A Amphipathic Peptides." *Biochemistry,* 34: 7955–7965.

Brouillette et al. (1995) Structural Models of Human Apolipoprotein A–1: Biochemica et Biophysica Acta 1256:103–129.

Van Lenten et al. (2001) "Acute Influenza A Infection Promotes Increased Macrophage Infiltration in the Artery Wall that is Prevented by Apolipoprotein A–1" Circulation 104(17):470, Abstract.

Van Lenten et al. (2002) "Influenza Infection Promotes Macrophage Traffic Into Arteries of Mice That is Prevented by D–4F, an Apolipoprotein A–1 Mimetic Peptide", Circulation 106:1127–1132.

Naghavi et al.(2003) "Influenza Infection Exerts Prominent Inflammatory and Thrombotic Effects on the Atherosclerotic Plaques of Aplolipoprotein E–Deficient Mice", Circulation 107:762–768.

Canadian Pharmacists Association, Starlix General Monograph. http://cpha.infinetcomm.com/content/hcp/tools/cps_cnp_updates/starlix.cfm (Not dated).

Starlix MC—Amino Acid Fact Sheet. http://www.starlix.com/media_center/content/pages/amino.htm. (Not dated).

Boffelli et al. (1997) "Reconstitution and Further Characterization of the Cholesterol Transport Activity of the Small-–Intestinal Brush Border Membrane" *Biochemistry* 36:10784–10792.

Bauer et al. (1982) "SMS 201–995: A Very Potent and Selective Octapeptide Analogue of Somatostatin with Prolonged Action" *Life Sciences* 31:1133–1140.

Datta et al. (2001) Effects of Increasing Hydrophobicity on the Physical–Chemical and Biological Properties of a Class A Amphipathic Helical Peptide. *J Lipid Research* 42:1096–1104.

Diederich et al. (2001) "Apolipoprotein AI and HDL$_3$ Inhibit Spreading of Primary Human Monocytes through a Mechanism that Involves Cholesterol Depletion and Regulation of CD42" *Atherosclerosis* 159:313–324.

Dooley et al. (1994) "An All D–Amino Acid Opioid Peptide with Central Analgesic Activity from a Combinatorial Library" *Science* 2019–2022.

Fricker et al. (1995) "Enteral Absorption of Octreotide: Modulation of Intestinal Permeability by Distinct Carbohydrates" *The Journal of Pharmacology and Experimental Therapeutics* 274:826–832.

Fuessl et al. (1987) "Oral Absroption of the Somatostatin Analogue SMS 201–995: Theoretical and Practial Implications" *Clinical Science* 72: 255–257.

Gurfinkel et al. (2002) "Influenza Vaccine Pilot Study in Acute Coronary Syndromes and Planned Percutaneous Coronary Interventions. The FLU Vaccination Acute Coronary Syndromes (FLUVACS) Study" *Circulation* 105:2143–2147.

Hamase et al. (2001) "Determination of Free D–Proline and D–Leucine in the Brains of Mutant Mice Lacking D–Amino Acid Oxidase Activity" *Analytical Biochemistry* 298:253–258.

Hardy et al. (2001) "An Automated High–Performance Liquid Chromatography Procedure for the Quantitation of L– and D–Amino Acids by Means of Stepwise Precolumn Derivatization" Analytical Biochemistry 291:297–299.

Hauser et al. (1998) "Identification of a Receptor Mediating Absorption of Dietary Cholesterol in the Intestine" *Biochemistry* 178423–17850.

Hyka et al. (2001) "Apolipoprotein A–I Inhibits the Production of Interleukin–1 ☐ and Tumor Necrosis Factor–☐ by Blocking Contact–Mediated Activation of Monocytes by T Lymphocytes" *Blood* 97:2381–2389.

Jones et al. (1992) "Computer Programs to Identify and Classify Amphipathic ☐ Helical Domains" *Journal of Lipid Research* 33:287–296.

Kullman et al. (1999) "Evaluation of the Enantiomeric Composition of Amino Acids in Tobacco" *Chirality* 11:669–673.

Lundin et al. (1986) "Absorption of Intragastrically Administered DDAVP in Conscious Dogs" *Life Sciences* 38:703–709.

Merrifield et al. (1995) "Retro and Retroenantio Analogs of Cecropin–Melittin Hybrids" *Proc Natl Acad Sci USA* 92: 3449–3453.

Navab et al. (2002) "Oral Administration of an Apo A–I Mimetic Peptide Synthesized from D–Amino Acids Dramatically Reduces Atherosclerosis in Mice Independent of Plasma Cholesterol" *Circulation* 105: 290–292.

Owens et al. (1990) "Apolipoprotein A–I and its Amphipathic Helix Peptide Analogues Inhibit Human Immunodeficiency Virus–Induced Syncytium Formation" *J Clin Invest* 86: 1142–1150.

Pappenheimer et al. (1994) "Intestinal Absorption and Excretion of Octapeptides Composed of D Amino Acids" *Proc Natl Acad Sci USA* 91: 1942–1945.

Peng et al. (2001) "Effects of L–glutamate, D–aspartate, and Monensin on Glycolytic and Oxidative Glucose Metabolism in Mouse Astrocyte Cultures: Further Evidence that Glutamate Uptake is Metabolically Driven by Oxidative Metabolism" *Neurochemistry International* 38:437–443.

Panizzutti et al. (2001) "A New Strategy to Decrease N–methyl–D–aspartate (NMDA) Receptor Coactivation: Inhibition of D–serine Synthesis by Converting Serine Racemase into an Eliminase" *PNAS* 98:5294–5299.

Segrest et al. (1992) "The Amphipathic Helix in the Exchangeable Apolipoproteins: A Review of Secondary Structure and Function" *J Lipid Research* 33:141–166.

Sing et al. (2000) "Innate Defences Against Viraemia" *Rev Med Virol* 10:395–403.

Srinivas et al. (1990) "Antivrial Effects of Apolipoprotein A–I and Its Synthetic Amphipathic Peptide Anlogs" *Virology* 176:48–57.

Tsao et al. (2001) "Hibernation–induction Peptide and Cell Death: [D–Ala$^2$,D–Leu$^5$]enkephalin Blocks Bax–related Apoptotic Processes" *European Journal of Pharmacology* 428:149–151.

SEQUENCE LISTING

```
<160> NUMBER OF SEQ ID NOS: 39

<210> SEQ ID NO 1
<211> LENGTH: 18
<212> TYPE: PRT
<213> ORGANISM: Artificial Sequence
<220> FEATURE:
<223> OTHER INFORMATION: synthetic peptide

<400> SEQUENCE: 1

Asp Trp Leu Lys Ala Phe Tyr Asp Lys Val Ala Glu Lys Leu Lys Glu
1               5                   10                  15

Ala Phe

<210> SEQ ID NO 2
<211> LENGTH: 18
<212> TYPE: PRT
<213> ORGANISM: Artificial Sequence
<220> FEATURE:
<223> OTHER INFORMATION: synthetic peptide
<221> NAME/KEY: misc_feature
<222> LOCATION: (1)..(1)
<223> OTHER INFORMATION: D is blocked with an acetyl
<221> NAME/KEY: misc_feature
<222> LOCATION: (18)..(18)
<223> OTHER INFORMATION: F is blocked with an amide

<400> SEQUENCE: 2

Asp Trp Leu Lys Ala Phe Tyr Asp Lys Val Ala Glu Lys Leu Lys Glu
1               5                   10                  15

Ala Phe

<210> SEQ ID NO 3
<211> LENGTH: 18
<212> TYPE: PRT
<213> ORGANISM: Artificial Sequence
<220> FEATURE:
<223> OTHER INFORMATION: synthetic peptide
<221> NAME/KEY: misc_feature
<222> LOCATION: (1)..(1)
<223> OTHER INFORMATION: D is blocked with an acetyl
<221> NAME/KEY: misc_feature
<222> LOCATION: (18)..(18)
<223> OTHER INFORMATION: F is blocked with an amide

<400> SEQUENCE: 3

Asp Trp Phe Lys Ala Phe Tyr Asp Lys Val Ala Glu Lys Leu Lys Glu
1               5                   10                  15

Ala Phe

<210> SEQ ID NO 4
<211> LENGTH: 18
<212> TYPE: PRT
<213> ORGANISM: Artificial Sequence
<220> FEATURE:
<223> OTHER INFORMATION: synthetic peptide
```

```
<221> NAME/KEY: misc_feature
<222> LOCATION: (1)..(1)
<223> OTHER INFORMATION: D is blocked with an acetyl
<221> NAME/KEY: misc_feature
<222> LOCATION: (18)..(18)
<223> OTHER INFORMATION: F is blocked with an amide

<400> SEQUENCE: 4

Asp Trp Leu Lys Ala Phe Tyr Asp Lys Val Ala Glu Lys Phe Lys Glu
1               5                   10                  15

Ala Phe

<210> SEQ ID NO 5
<211> LENGTH: 18
<212> TYPE: PRT
<213> ORGANISM: Artificial Sequence
<220> FEATURE:
<223> OTHER INFORMATION: synthetic peptide
<221> NAME/KEY: misc_feature
<222> LOCATION: (1)..(1)
<223> OTHER INFORMATION: D is blocked with an acetyl
<221> NAME/KEY: misc_feature
<222> LOCATION: (18)..(18)
<223> OTHER INFORMATION: F is blocked with an amide

<400> SEQUENCE: 5

Asp Trp Phe Lys Ala Phe Tyr Asp Lys Val Ala Glu Lys Phe Lys Glu
1               5                   10                  15

Ala Phe

<210> SEQ ID NO 6
<211> LENGTH: 18
<212> TYPE: PRT
<213> ORGANISM: Artificial Sequence
<220> FEATURE:
<223> OTHER INFORMATION: synthetic peptide
<221> NAME/KEY: misc_feature
<222> LOCATION: (1)..(1)
<223> OTHER INFORMATION: D is blocked with an acetyl
<221> NAME/KEY: misc_feature
<222> LOCATION: (18)..(18)
<223> OTHER INFORMATION: F is blocked with an amide

<400> SEQUENCE: 6

Asp Trp Leu Lys Ala Phe Tyr Asp Lys Phe Phe Glu Lys Phe Lys Glu
1               5                   10                  15

Phe Phe

<210> SEQ ID NO 7
<211> LENGTH: 18
<212> TYPE: PRT
<213> ORGANISM: Artificial Sequence
<220> FEATURE:
<223> OTHER INFORMATION: synthetic peptide
<221> NAME/KEY: misc_feature
<222> LOCATION: (1)..(1)
<223> OTHER INFORMATION: D is blocked with an acetyl
<221> NAME/KEY: misc_feature
<222> LOCATION: (18)..(18)
<223> OTHER INFORMATION: F is blocked with an amide

<400> SEQUENCE: 7

Asp Trp Phe Lys Ala Phe Tyr Asp Lys Phe Phe Glu Lys Phe Lys Glu
1               5                   10                  15

Phe Phe

<210> SEQ ID NO 8
```

```
<211> LENGTH: 18
<212> TYPE: PRT
<213> ORGANISM: Artificial Sequence
<220> FEATURE:
<223> OTHER INFORMATION: synthetic peptide
<221> NAME/KEY: misc_feature
<222> LOCATION: (1)..(1)
<223> OTHER INFORMATION: D is blocked with an acetyl
<221> NAME/KEY: misc_feature
<222> LOCATION: (18)..(18)
<223> OTHER INFORMATION: F is blocked with an amide

<400> SEQUENCE: 8

Asp Trp Leu Lys Ala Phe Tyr Asp Lys Val Ala Glu Lys Phe Lys Glu
1               5                   10                  15

Ala Phe

<210> SEQ ID NO 9
<211> LENGTH: 18
<212> TYPE: PRT
<213> ORGANISM: Artificial Sequence
<220> FEATURE:
<223> OTHER INFORMATION: synthetic peptide
<221> NAME/KEY: misc_feature
<222> LOCATION: (1)..(1)
<223> OTHER INFORMATION: D is blocked with an acetyl
<221> NAME/KEY: misc_feature
<222> LOCATION: (18)..(18)
<223> OTHER INFORMATION: F is blocked with an amide

<400> SEQUENCE: 9

Asp Trp Leu Lys Ala Phe Tyr Asp Lys Val Ala Glu Lys Leu Lys Glu
1               5                   10                  15

Phe Phe

<210> SEQ ID NO 10
<211> LENGTH: 18
<212> TYPE: PRT
<213> ORGANISM: Artificial Sequence
<220> FEATURE:
<223> OTHER INFORMATION: synthetic peptide
<221> NAME/KEY: misc_feature
<222> LOCATION: (1)..(1)
<223> OTHER INFORMATION: D is blocked with an acetyl
<221> NAME/KEY: misc_feature
<222> LOCATION: (18)..(18)
<223> OTHER INFORMATION: F is blocked with an amide

<400> SEQUENCE: 10

Asp Trp Leu Lys Ala Phe Tyr Asp Lys Val Phe Glu Lys Phe Lys Glu
1               5                   10                  15

Ala Phe

<210> SEQ ID NO 11
<211> LENGTH: 18
<212> TYPE: PRT
<213> ORGANISM: Artificial Sequence
<220> FEATURE:
<223> OTHER INFORMATION: synthetic peptide
<221> NAME/KEY: misc_feature
<222> LOCATION: (1)..(1)
<223> OTHER INFORMATION: D is blocked with an acetyl
<221> NAME/KEY: misc_feature
<222> LOCATION: (18)..(18)
<223> OTHER INFORMATION: F is blocked with an amide

<400> SEQUENCE: 11

Asp Trp Leu Lys Ala Phe Tyr Asp Lys Val Phe Glu Lys Leu Lys Glu
1               5                   10                  15
```

Phe Phe

<210> SEQ ID NO 12
<211> LENGTH: 18
<212> TYPE: PRT
<213> ORGANISM: Artificial Sequence
<220> FEATURE:
<223> OTHER INFORMATION: synthetic peptide
<221> NAME/KEY: misc_feature
<222> LOCATION: (1)..(1)
<223> OTHER INFORMATION: D is blocked with an acetyl
<221> NAME/KEY: misc_feature
<222> LOCATION: (18)..(18)
<223> OTHER INFORMATION: F is blocked with an amide

<400> SEQUENCE: 12

Asp Trp Leu Lys Ala Phe Tyr Asp Lys Val Ala Glu Lys Phe Lys Glu
1               5                   10                  15

Phe Phe

<210> SEQ ID NO 13
<211> LENGTH: 18
<212> TYPE: PRT
<213> ORGANISM: Artificial Sequence
<220> FEATURE:
<223> OTHER INFORMATION: synthetic peptide
<221> NAME/KEY: misc_feature
<222> LOCATION: (1)..(1)
<223> OTHER INFORMATION: D is blocked with an acetyl
<221> NAME/KEY: misc_feature
<222> LOCATION: (18)..(18)
<223> OTHER INFORMATION: F is blocked with an amide

<400> SEQUENCE: 13

Asp Trp Leu Lys Ala Phe Tyr Asp Lys Val Phe Glu Lys Phe Lys Glu
1               5                   10                  15

Phe Phe

<210> SEQ ID NO 14
<211> LENGTH: 18
<212> TYPE: PRT
<213> ORGANISM: Artificial Sequence
<220> FEATURE:
<223> OTHER INFORMATION: synthetic peptide
<221> NAME/KEY: misc_feature
<222> LOCATION: (1)..(1)
<223> OTHER INFORMATION: E is blocked with an acetyl
<221> NAME/KEY: misc_feature
<222> LOCATION: (18)..(18)
<223> OTHER INFORMATION: F is blocked with an amide

<400> SEQUENCE: 14

Glu Trp Leu Lys Leu Phe Tyr Glu Lys Val Leu Glu Lys Phe Lys Glu
1               5                   10                  15

Ala Phe

<210> SEQ ID NO 15
<211> LENGTH: 18
<212> TYPE: PRT
<213> ORGANISM: Artificial Sequence
<220> FEATURE:
<223> OTHER INFORMATION: synthetic peptide
<221> NAME/KEY: misc_feature
<222> LOCATION: (1)..(1)
<223> OTHER INFORMATION: E is blocked with an acetyl
<221> NAME/KEY: misc_feature
<222> LOCATION: (18)..(18)
<223> OTHER INFORMATION: F is blocked with an amide

```
<400> SEQUENCE: 15

Glu Trp Leu Lys Ala Phe Tyr Asp Lys Val Ala Glu Lys Phe Lys Glu
1               5                   10                  15

Ala Phe

<210> SEQ ID NO 16
<211> LENGTH: 18
<212> TYPE: PRT
<213> ORGANISM: Artificial Sequence
<220> FEATURE:
<223> OTHER INFORMATION: synthetic peptide
<221> NAME/KEY: misc_feature
<222> LOCATION: (1)..(1)
<223> OTHER INFORMATION: E is blocked with an acetyl
<221> NAME/KEY: misc_feature
<222> LOCATION: (18)..(18)
<223> OTHER INFORMATION: F is blocked with an amide

<400> SEQUENCE: 16

Glu Trp Leu Lys Ala Phe Tyr Asp Lys Val Ala Glu Lys Leu Lys Glu
1               5                   10                  15

Phe Phe

<210> SEQ ID NO 17
<211> LENGTH: 18
<212> TYPE: PRT
<213> ORGANISM: Artificial Sequence
<220> FEATURE:
<223> OTHER INFORMATION: synthetic peptide
<221> NAME/KEY: misc_feature
<222> LOCATION: (1)..(1)
<223> OTHER INFORMATION: E is blocked with an acetyl
<221> NAME/KEY: misc_feature
<222> LOCATION: (18)..(18)
<223> OTHER INFORMATION: F is blocked with an amide

<400> SEQUENCE: 17

Glu Trp Leu Lys Ala Phe Tyr Asp Lys Val Phe Glu Lys Phe Lys Glu
1               5                   10                  15

Ala Phe

<210> SEQ ID NO 18
<211> LENGTH: 18
<212> TYPE: PRT
<213> ORGANISM: Artificial Sequence
<220> FEATURE:
<223> OTHER INFORMATION: synthetic peptide
<221> NAME/KEY: misc_feature
<222> LOCATION: (1)..(1)
<223> OTHER INFORMATION: E is blocked with an acetyl
<221> NAME/KEY: misc_feature
<222> LOCATION: (18)..(18)
<223> OTHER INFORMATION: F is blocked with an amide

<400> SEQUENCE: 18

Glu Trp Leu Lys Ala Phe Tyr Asp Lys Val Phe Glu Lys Leu Lys Glu
1               5                   10                  15

Phe Phe

<210> SEQ ID NO 19
<211> LENGTH: 18
<212> TYPE: PRT
<213> ORGANISM: Artificial Sequence
<220> FEATURE:
<223> OTHER INFORMATION: synthetic peptide
<221> NAME/KEY: misc_feature
```

```
<222> LOCATION: (1)..(1)
<223> OTHER INFORMATION: E is blocked with an acetyl
<221> NAME/KEY: misc_featureUNSURE
<222> LOCATION: (18)..(18)
<223> OTHER INFORMATION: F is blocked with an amide

<400> SEQUENCE: 19

Glu Trp Leu Lys Ala Phe Tyr Asp Lys Val Ala Glu Lys Phe Lys Glu
1               5                   10                  15

Phe Phe

<210> SEQ ID NO 20
<211> LENGTH: 18
<212> TYPE: PRT
<213> ORGANISM: Artificial Sequence
<220> FEATURE:
<223> OTHER INFORMATION: synthetic peptide
<221> NAME/KEY: misc_feature
<222> LOCATION: (1)..(1)
<223> OTHER INFORMATION: E is blocked with an acetyl
<221> NAME/KEY: misc_feature
<222> LOCATION: (18)..(18)
<223> OTHER INFORMATION: F is blocked with an amide

<400> SEQUENCE: 20

Glu Trp Leu Lys Ala Phe Tyr Asp Lys Val Phe Glu Lys Phe Lys Glu
1               5                   10                  15

Phe Phe

<210> SEQ ID NO 21
<211> LENGTH: 14
<212> TYPE: PRT
<213> ORGANISM: Artificial Sequence
<220> FEATURE:
<223> OTHER INFORMATION: synthetic peptide
<221> NAME/KEY: misc_feature
<222> LOCATION: (1)..(1)
<223> OTHER INFORMATION: A is blocked with an acetyl
<221> NAME/KEY: misc_feature
<222> LOCATION: (14)..(14)
<223> OTHER INFORMATION: F is blocked with an amide

<400> SEQUENCE: 21

Ala Phe Tyr Asp Lys Val Ala Glu Lys Leu Lys Glu Ala Phe
1               5                   10

<210> SEQ ID NO 22
<211> LENGTH: 14
<212> TYPE: PRT
<213> ORGANISM: Artificial Sequence
<220> FEATURE:
<223> OTHER INFORMATION: synthetic peptide
<221> NAME/KEY: misc_feature
<222> LOCATION: (1)..(1)
<223> OTHER INFORMATION: A is blocked with an acetyl
<221> NAME/KEY: misc_feature
<222> LOCATION: (14)..(14)
<223> OTHER INFORMATION: F is blocked with an amide

<400> SEQUENCE: 22

Ala Phe Tyr Asp Lys Val Ala Glu Lys Phe Lys Glu Ala Phe
1               5                   10

<210> SEQ ID NO 23
<211> LENGTH: 14
<212> TYPE: PRT
<213> ORGANISM: Artificial Sequence
<220> FEATURE:
<223> OTHER INFORMATION: synthetic peptide
```

```
<221> NAME/KEY: misc_feature
<222> LOCATION: (1)..(1)
<223> OTHER INFORMATION: A is blocked with an acetyl
<221> NAME/KEY: misc_feature
<222> LOCATION: (14)..(14)
<223> OTHER INFORMATION: F is blocked with an amide

<400> SEQUENCE: 23

Ala Phe Tyr Asp Lys Val Ala Glu Lys Phe Lys Glu Ala Phe
1               5                  10

<210> SEQ ID NO 24
<211> LENGTH: 14
<212> TYPE: PRT
<213> ORGANISM: Artificial Sequence
<220> FEATURE:
<223> OTHER INFORMATION: synthetic peptide
<221> NAME/KEY: misc_feature
<222> LOCATION: (1)..(1)
<223> OTHER INFORMATION: A is blocked with an acetyl
<221> NAME/KEY: misc_feature
<222> LOCATION: (14)..(14)
<223> OTHER INFORMATION: F is blocked with an amide

<400> SEQUENCE: 24

Ala Phe Tyr Asp Lys Phe Phe Glu Lys Phe Lys Glu Phe Phe
1               5                  10

<210> SEQ ID NO 25
<211> LENGTH: 14
<212> TYPE: PRT
<213> ORGANISM: Artificial Sequence
<220> FEATURE:
<223> OTHER INFORMATION: synthetic peptide
<221> NAME/KEY: misc_feature
<222> LOCATION: (1)..(1)
<223> OTHER INFORMATION: A is blocked with an acetyl
<221> NAME/KEY: misc_feature
<222> LOCATION: (14)..(14)
<223> OTHER INFORMATION: F is blocked with an amide

<400> SEQUENCE: 25

Ala Phe Tyr Asp Lys Phe Phe Glu Lys Phe Lys Glu Phe Phe
1               5                  10

<210> SEQ ID NO 26
<211> LENGTH: 14
<212> TYPE: PRT
<213> ORGANISM: Artificial Sequence
<220> FEATURE:
<223> OTHER INFORMATION: synthetic peptide
<221> NAME/KEY: misc_feature
<222> LOCATION: (1)..(1)
<223> OTHER INFORMATION: A is blocked with an acetyl
<221> NAME/KEY: misc_feature
<222> LOCATION: (14)..(14)
<223> OTHER INFORMATION: F is blocked with an amide

<400> SEQUENCE: 26

Ala Phe Tyr Asp Lys Val Ala Glu Lys Phe Lys Glu Ala Phe
1               5                  10

<210> SEQ ID NO 27
<211> LENGTH: 14
<212> TYPE: PRT
<213> ORGANISM: Artificial Sequence
<220> FEATURE:
<223> OTHER INFORMATION: synthetic peptide
<221> NAME/KEY: misc_feature
<222> LOCATION: (1)..(1)
<223> OTHER INFORMATION: A is blocked with an acetyl
```

```
<221> NAME/KEY: misc_feature
<222> LOCATION: (14)..(14)
<223> OTHER INFORMATION: F is blocked with an amide

<400> SEQUENCE: 27

Ala Phe Tyr Asp Lys Val Ala Glu Lys Leu Lys Glu Phe Phe
1               5                   10

<210> SEQ ID NO 28
<211> LENGTH: 14
<212> TYPE: PRT
<213> ORGANISM: Artificial Sequence
<220> FEATURE:
<223> OTHER INFORMATION: synthetic peptide
<221> NAME/KEY: misc_feature
<222> LOCATION: (1)..(1)
<223> OTHER INFORMATION: A is blocked with an acetyl
<221> NAME/KEY: misc_feature
<222> LOCATION: (14)..(14)
<223> OTHER INFORMATION: F is blocked with an amide

<400> SEQUENCE: 28

Ala Phe Tyr Asp Lys Val Phe Glu Lys Phe Lys Glu Ala Phe
1               5                   10

<210> SEQ ID NO 29
<211> LENGTH: 14
<212> TYPE: PRT
<213> ORGANISM: Artificial Sequence
<220> FEATURE:
<223> OTHER INFORMATION: synthetic peptide
<221> NAME/KEY: misc_feature
<222> LOCATION: (1)..(1)
<223> OTHER INFORMATION: A is blocked with an acetyl
<221> NAME/KEY: misc_feature
<222> LOCATION: (14)..(14)
<223> OTHER INFORMATION: F is blocked with an amide

<400> SEQUENCE: 29

Ala Phe Tyr Asp Lys Val Phe Glu Lys Leu Lys Glu Phe Phe
1               5                   10

<210> SEQ ID NO 30
<211> LENGTH: 14
<212> TYPE: PRT
<213> ORGANISM: Artificial Sequence
<220> FEATURE:
<223> OTHER INFORMATION: synthetic peptide
<221> NAME/KEY: misc_feature
<222> LOCATION: (1)..(1)
<223> OTHER INFORMATION: A is blocked with an acetyl
<221> NAME/KEY: misc_feature
<222> LOCATION: (14)..(14)
<223> OTHER INFORMATION: F is blocked with an amide

<400> SEQUENCE: 30

Ala Phe Tyr Asp Lys Val Ala Glu Lys Phe Lys Glu Phe Phe
1               5                   10

<210> SEQ ID NO 31
<211> LENGTH: 14
<212> TYPE: PRT
<213> ORGANISM: Artificial Sequence
<220> FEATURE:
<223> OTHER INFORMATION: synthetic peptide
<221> NAME/KEY: misc_feature
<222> LOCATION: (1)..(1)
<223> OTHER INFORMATION: K is blocked with an acetyl
<221> NAME/KEY: misc_feature
<222> LOCATION: (14)..(14)
<223> OTHER INFORMATION: F is blocked with an amide
```

<400> SEQUENCE: 31

Lys Ala Phe Tyr Asp Lys Val Phe Glu Lys Phe Lys Glu Phe
1               5                   10

<210> SEQ ID NO 32
<211> LENGTH: 14
<212> TYPE: PRT
<213> ORGANISM: Artificial Sequence
<220> FEATURE:
<223> OTHER INFORMATION: synthetic peptide
<221> NAME/KEY: misc_feature
<222> LOCATION: (1)..(1)
<223> OTHER INFORMATION: L is blocked with an acetyl
<221> NAME/KEY: misc_feature
<222> LOCATION: (14)..(14)
<223> OTHER INFORMATION: F is blocked with an amide

<400> SEQUENCE: 32

Leu Phe Tyr Glu Lys Val Leu Glu Lys Phe Lys Glu Ala Phe
1               5                   10

<210> SEQ ID NO 33
<211> LENGTH: 14
<212> TYPE: PRT
<213> ORGANISM: Artificial Sequence
<220> FEATURE:
<223> OTHER INFORMATION: synthetic peptide
<221> NAME/KEY: misc_feature
<222> LOCATION: (1)..(1)
<223> OTHER INFORMATION: A is blocked with an acetyl
<221> NAME/KEY: misc_feature
<222> LOCATION: (14)..(14)
<223> OTHER INFORMATION: F is blocked with an amide

<400> SEQUENCE: 33

Ala Phe Tyr Asp Lys Val Ala Glu Lys Phe Lys Glu Ala Phe
1               5                   10

<210> SEQ ID NO 34
<211> LENGTH: 14
<212> TYPE: PRT
<213> ORGANISM: Artificial Sequence
<220> FEATURE:
<223> OTHER INFORMATION: synthetic peptide
<221> NAME/KEY: misc_feature
<222> LOCATION: (1)..(1)
<223> OTHER INFORMATION: A is blocked with an acetyl
<221> NAME/KEY: misc_feature
<222> LOCATION: (14)..(14)
<223> OTHER INFORMATION: F is blocked with an amide

<400> SEQUENCE: 34

Ala Phe Tyr Asp Lys Val Ala Glu Lys Leu Lys Glu Phe Phe
1               5                   10

<210> SEQ ID NO 35
<211> LENGTH: 14
<212> TYPE: PRT
<213> ORGANISM: Artificial Sequence
<220> FEATURE:
<223> OTHER INFORMATION: synthetic peptide
<221> NAME/KEY: misc_feature
<222> LOCATION: (1)..(1)
<223> OTHER INFORMATION: A is blocked with an acetyl
<221> NAME/KEY: misc_feature
<222> LOCATION: (14)..(14)
<223> OTHER INFORMATION: F is blocked with an amide

<400> SEQUENCE: 35

```
Ala Phe Tyr Asp Lys Val Phe Glu Lys Phe Lys Glu Ala Phe
1               5                   10

<210> SEQ ID NO 36
<211> LENGTH: 14
<212> TYPE: PRT
<213> ORGANISM: Artificial Sequence
<220> FEATURE:
<223> OTHER INFORMATION: synthetic peptide
<221> NAME/KEY: misc_feature
<222> LOCATION: (1)..(1)
<223> OTHER INFORMATION: A is blocked with an acetyl
<221> NAME/KEY: misc_feature
<222> LOCATION: (14)..(14)
<223> OTHER INFORMATION: F is blocked with an amide

<400> SEQUENCE: 36

Ala Phe Tyr Asp Lys Val Phe Glu Lys Leu Lys Glu Phe Phe
1               5                   10

<210> SEQ ID NO 37
<211> LENGTH: 14
<212> TYPE: PRT
<213> ORGANISM: Artificial Sequence
<220> FEATURE:
<223> OTHER INFORMATION: synthetic peptide
<221> NAME/KEY: misc_feature
<222> LOCATION: (1)..(1)
<223> OTHER INFORMATION: A is blocked with an acetyl
<221> NAME/KEY: misc_feature
<222> LOCATION: (14)..(14)
<223> OTHER INFORMATION: F is blocked with an amide

<400> SEQUENCE: 37

Ala Phe Tyr Asp Lys Val Ala Glu Lys Phe Lys Glu Phe Phe
1               5                   10

<210> SEQ ID NO 38
<211> LENGTH: 14
<212> TYPE: PRT
<213> ORGANISM: Artificial Sequence
<220> FEATURE:
<223> OTHER INFORMATION: synthetic peptide
<221> NAME/KEY: misc_feature
<222> LOCATION: (1)..(1)
<223> OTHER INFORMATION: A is blocked with an acetyl
<221> NAME/KEY: misc_feature
<222> LOCATION: (14)..(14)
<223> OTHER INFORMATION: F is blocked with an amide

<400> SEQUENCE: 38

Ala Phe Tyr Asp Lys Val Phe Glu Lys Phe Lys Glu Phe Phe
1               5                   10

<210> SEQ ID NO 39
<211> LENGTH: 18
<212> TYPE: PRT
<213> ORGANISM: Artificial Sequence
<220> FEATURE:
<223> OTHER INFORMATION: synthetic peptide
<221> NAME/KEY: misc_feature
<222> LOCATION: (1)..(1)
<223> OTHER INFORMATION: X is aspartic acid, glutamic, or homologues or
      analogues thereof
<221> NAME/KEY: misc_feature
<222> LOCATION: (8)..(8)
<223> OTHER INFORMATION: X is aspartic acid, glutamic, or homologues or
      analogues thereof
<221> NAME/KEY: misc_feature
<222> LOCATION: (12)..(12)
<223> OTHER INFORMATION: X is aspartic acid, glutamic, or homologues or
      analogues thereof
```

```
<221> NAME/KEY: misc_feature
<222> LOCATION: (16)..(16)
<223> OTHER INFORMATION: X is aspartic acid, glutamic, or homologues or
      analogues thereof
<221> NAME/KEY: misc_feature
<222> LOCATION: (2)..(3)
<223> OTHER INFORMATION: X is tryptophan, phenylalanine, alanine,
      leucine, tyrosine, isoleucine, valine, or alpha-maphthylalanine, or
      homologues or analogues thereof
<221> NAME/KEY: misc_feature
<222> LOCATION: (6)..(7)
<223> OTHER INFORMATION: X is tryptophan, phenylalanine, alanine,
      leucine, tyrosine, isoleucine, valine, or alpha-maphthylalanine, or
      homologues or analogues thereof
<221> NAME/KEY: misc_feature
<222> LOCATION: (10)..(11)
<223> OTHER INFORMATION: X is tryptophan, phenylalanine, alanine,
      leucine, tyrosine, isoleucine, valine, or alpha-maphthylalanine, or
      homologues or analogues thereof
<221> NAME/KEY: misc_feature
<222> LOCATION: (14)..(14)
<223> OTHER INFORMATION: X is tryptophan, phenylalanine, alanine,
      leucine, tyrosine, isoleucine, valine, or alpha-maphthylalanine, or
      homologues or analogues thereof
<221> NAME/KEY: misc_feature
<222> LOCATION: (17)..(18)
<223> OTHER INFORMATION: X is tryptophan, phenylalanine, alanine,
      leucine, tyrosine, isoleucine, valine, or alpha-maphthylalanine, or
      homologues or analogues thereof
<221> NAME/KEY: misc_feature
<222> LOCATION: (4)..(4)
<223> OTHER INFORMATION: X is lysine or arginine
<221> NAME/KEY: misc_feature
<222> LOCATION: (9)..(9)
<223> OTHER INFORMATION: X is lysine or arginine
<221> NAME/KEY: misc_feature
<222> LOCATION: (13)..(13)
<223> OTHER INFORMATION: X is lysine or arginine
<221> NAME/KEY: misc_feature
<222> LOCATION: (15)..(15)
<223> OTHER INFORMATION: X is lysine or arginine
<221> NAME/KEY: misc_feature
<222> LOCATION: (5)..(5)
<223> OTHER INFORMATION: X is serine, threonine, alanine, glycine,
      histidine, or homologues or analogues thereof

<400> SEQUENCE: 39

Xaa Xaa Xaa Xaa Xaa Xaa Xaa Xaa Xaa Xaa Xaa Xaa Xaa Xaa Xaa Xaa
1               5                   10                  15

Xaa Xaa
```

ORALLY ADMINISTERED PEPTIDES TO AMELIORATE ATHEROSCLEROSIS

STATEMENT AS TO RIGHTS TO INVENTIONS MADE UNDER FEDERALLY SPONSORED RESEARCH AND DEVELOPMENT

This work was supported by United States Public Health Service and National Heart, Lung, and Blood Institute Grants HL30568 and HL34343. The Government of the United States of America may have certain rights in this invention.

FIELD OF THE INVENTION

This invention relates to the field of atherosclerosis. In particular, this invention pertains to the identification of a class of peptides that are orally administrable and that ameliorate one or more symptoms of atherosclerosis.

BACKGROUND OF THE INVENTION

Cardiovascular disease is a leading cause of morbidity and mortality, particularly in the United States and in Western European countries. Several causative factors are implicated in the development of cardiovascular disease including hereditary predisposition to the disease, gender, lifestyle factors such as smoking and diet, age, hypertension, and hyperlipidemia, including hypercholesterolemia. Several of these factors, particularly hyperlipidemia and hypercholesteremia (high blood cholesterol concentrations) provide a significant risk factor associated with atherosclerosis.

Cholesterol is present in the blood as free and esterified cholesterol within lipoprotein particles, commonly known as chylomicrons, very low density lipoproteins (VLDLs), low density lipoproteins (LDLs), and high density lipoproteins (HDLs). Concentration of total cholesterol in the blood is influenced by (1) absorption of cholesterol from the digestive tract, (2) synthesis of cholesterol from dietary constituents such as carbohydrates, proteins, fats and ethanol, and (3) removal of cholesterol from blood by tissues, especially the liver, and subsequent conversion of the cholesterol to bile acids, steroid hormones, and biliary cholesterol.

Maintenance of blood cholesterol concentrations is influenced by both genetic and environmental factors. Genetic factors include concentration of rate-limiting enzymes in cholesterol biosynthesis, concentration of receptors for low density lipoproteins in the liver, concentration of rate-limiting enzymes for conversion of cholesterols bile acids, rates of synthesis and secretion of lipoproteins and gender of person. Environmental factors influencing the hemostasis of blood cholesterol concentration in humans include dietary composition, incidence of smoking, physical activity, and use of a variety of pharmaceutical agents. Dietary variables include amount and type of fat (saturated and polyunsaturated fatty acids), amount of cholesterol, amount and type of fiber, and perhaps amounts of vitamins such as vitamin C and D and minerals such as calcium.

Epidemiological studies show an inverse correlation of high density lipoprotein (HDL) and apolipoprotein (apo) A-I levels with the occurrence of atherosclerotic events (Wilson et al. (1988) *Arteriosclerosis* 8: 737–741). Injection of HDL into rabbits fed an atherogenic diet has been shown to inhibit atherosclerotic lesion formation (Badimon et al. (1990) *J. Clin. Invest.* 85: 1234–1241).

Human apo A-I has been a subject of intense study because of its anti-atherogenic properties. Exchangeable apolipoproteins, including apo A-I, possess lipid-associating domains (Brouillette and Anantharamaiah (1995) *Biochim. Biophys. Acta* 1256:103–129; Segrest et al. (1974) *FEBS Lett.* 38: :247–253). Apo A-I has been postulated to possess eight tandem repeating 22 mer sequences, most of which have the potential to form class A amphipathic helical structures (Segrest et al. (1974) *FEBS Lett.* 38: 247–253). Characteristics of the class A amphipathic helix include the presence of positively charged residues at the polar-nonpolar interface and negatively charged residues at the center of the polar face (Segrest et al. (1974) FEBS Lett. 38: 247–253; Segrest et al. (1990) *Proteins: Structure, Function, and Genetics* 8: 103–117). Apo A-I has been shown to strongly associate with phospholipids to form complexes and to promote cholesterol efflux from cholesterol-enriched cells. The delivery and maintenance of serum levels of apo A-I to effectively mitigate one or more symptoms of atherosclerosis has heretofore proven elusive.

SUMMARY OF THE INVENTION

This invention provides novel peptides administration of which mitigate one or more symptoms of atherosclerosis. In particular, it was a discovery of this invention that peptides comprising a class A amphipathic helix when formulated with "D" amino acid residue(s) and/or having protected amino and carboxyl termini can be orally administered to an organism, are readily taken up and delivered to the serum, and are effective to mitigate one or more symptoms of atherosclerosis.

Thus, in one embodiment, this invention provides a peptide that ameliorates a symptom of atherosclerosis, where the peptide ranges in length from about 10 to about 30 amino acids, comprises at least one class A amphipathic helix, comprises at least one "D" amino acid residue, protects a phospholipid against oxidation by an oxidizing agent, and is not the D-18A peptide (e.g. D-W-L-K-A-F-Y-D-K-V-A-E-K-L-K-E-A-F (SEQ ID NO: 1) having all D form amino acid residues). In particularly preferred embodiments, the peptide further comprises a protecting group coupled to the amino and/or carboxyl terminus. Preferred protecting groups include, but are not limited to acetyl, amide, and 3 to 20 carbon alkyl groups, Fmoc, Tboc, 9-fluoreneacetyl group, 1-fluorenecarboxylic group, 9-fluorenecarboxylic group, 9-fluorenone-1-carboxylic group, benzyloxycarbonyl, Xanthyl (Xan), Trityl (Trt), 4-methyltrityl (Mtt), 4-methoxytrityl (Mmt), 4-methoxy-2,3,6-trimethyl-benzenesulphonyl (Mtr), Mesitylene-2-sulphonyl (Mts), 4,4-dimethoxybenzhydryl (Mbh), Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl, (Bz), 3-nitro-2-pyridinesulphenyl (Npys), 1-(4,4-dimethyl-2,6-diaxocyclohexylidene)ethyl (Dde), 2,6-dichlorobenzyl (2,6-DiCl-Bzl), 2-chlorobenzyloxycarbonyl (2-Cl-Z), 2-bromobenzyloxycarbonyl (2-Br-Z), Benzyloxymethyl (Bom), t-butoxycarbonyl (Boc), cyclohexyloxy (cHxO), t-butoxymethyl (Bum), t-butoxy (tBuO), t-Butyl (tBu), Acetyl (Ac), and Trifluoroacetyl (TFA). In certain particularly preferred embodiments the peptide further comprises a first protecting group coupled to the amino terminus and a second protecting group coupled to the carboxyl terminus. Particularly preferred peptides comprise greater than about 50% amino acid sequence identity with human or mouse apo A-I1 or with the polypeptide encoded by the. exon encoding a class A amphipathic helix of human or mouse apo A-I1. In certain preferred embodiments, at least 50%, more preferably at least 75%, and most preferably at least 90% and even 100% of the enantiomeric amino acids are "D" amino acids.

The peptide may be combined with a pharmacologically acceptable excipient (e.g. an excipient suitable for oral administration to a mammal).

In certain particularly preferred embodiments, the peptide comprises one or more of the following amino acid sequences: D-W-L-K-A-F-Y-D-K-V-A-E-K-L-K-E-A-F (SEQ ID NO: 2), D-W-F-K-A-F-Y-D-K-V-A-E-K-L-K-E-A-F (SEQ-ID-NO:3), D-W-L-K-A-F-Y-D-K-V-A-E-K-F-K-E-A-F (SEQ-ID-NO:4), D-W-F-K-A-F-Y-D-K-V-A-E-K-F-K-E-A-F(SEQ-ID-NO:5), D-W-L-K-A-F-Y-D-K-F-F-E-K-F-K-E-F-F (SEQ-ID-NO:6), D-W-F-K-A-F-Y-D-K-F-F-E-K-F-K-E-F-F (SEQ-ID-NO:7), D-W-L-K-A-F-Y-D-K-V-A-E-K-F-K-E-A-F (SEQ-ID-NO:8), D-W-L-K-A-F-Y-D-K-V-A-E-K-L-K-E-F-F (SEQ-ID-NO:9), D-W-L-K-A-F-Y-D-K-V-F-E-K-F-K-E-A-F (SEQ-ID-NO:10), D-W-L-K-A-F-Y-D-K-V-F-E-K-L-K-E-F-F (SEQ-ID-NO:11), D-W-L-K-A-F-Y-D-K-V-A-E-K-F-K-E-F-F (SEQ-ID-NO:12), D-W-L-K-A-F-Y-D-K-V-F-E-K-F-K-E-F-F (SEQ-ID-NO:13), E-W-L-K-L-F-Y-E-K-V-L-E-K-F-K-E-A-F (SEQ-ID-NO:14), E-W-L-K-A-F-Y-D-K-V-A-E-K-F-K-E-A-F (SEQ-ID-NO:15), E-W-L-K-A-F-Y-D-K-V-A-E-K-L-K-E-F-F (SEQ-ID-NO:16), E-W-L-K-A-F-Y-D-K-V-F-E-K-F-K-E-A-F (SEQ-ID-NO:17), E-W-L-K-A-F-Y-D-K-V-F-E-K-L-K-E-F-F (SEQ-ID-NO:18), E-W-L-K-A-F-Y-D-K-V-A-E-K-F-K-E-F-F (SEQ-ID-NO:19), E-W-L-K-A-F-Y-D-K-V-F-E-K-F-K-E-F-F (SEQ ID NO:20), A-F-Y-D-K-V-A-E-K-L-K-E-A-F (SEQ ID NO:21), A-F-Y-D-K-V-A-E-K-F-K-E-A-F (SEQ ID NO:22), A-F-Y-D-K-V-A-E-K-F-K-E-A-F (SEQ ID NO:23), A-F-Y-D-K-F-F-E-K-F-K-E-F-F (SEQ ID NO:24), A-F-Y-D-K-F-F-E-K-F-K-E-F-F (SEQ ID NO:25), A-F-Y-D-K-V-A-E-K-F-K-E-A-F (SEQ ID NO:26), A-F-Y-D-K-V-A-E-K-L-K-E-F-F (SEQ ID NO:27), A-F-Y-D-K-V-F-E-K-F-K-E-A-F (SEQ ID NO:28), A-F-Y-D -K-V-F-E-K-L-K-E-F-F (SEQ ID NO:29), A-F-Y-D-K-V-A-E-K-F-K-E-F-F (SEQ ID NO:30), K-A-F-Y-D-K-V-F-E-K-F-K-E-F (SEQ ID NO:31), L-F-Y-E-K-V-L-E-K-F-K -E-A-F (SEQ ID NO:32), A-F-Y-D-K-V-A-E-K-F-K-E-A-F (SEQ ID NO:33), A-F-Y-D-K-V-A-E-K-L-K-E-F-F (SEQ ID NO:34), A-F-Y-D-K-V-F-E-K-F-K-E-A-F (SEQ ID NO:35), A-F-Y-D-K-V-F-E-K-L-K-E-F-F (SEQ ID NO:36), A-F-Y-D-K-V-A-E-K-F-K-E-F-F (SEQ ID NO:37), A-F-Y-D-K-V-F-E-K-F-K-E-F-F (SEQ ID NO:38), and/or the above sequences comprising amino acid analogs. The enantiomeric amino acids of such sequences preferably comprise at least one "D" amino acid. In certain preferred embodiments, at least 50%, more preferably at least 75%, and most preferably at least 90% and even 100% of the enantiomeric amino acids are "D" amino acids as described herein.

Such peptides can also include a protecting group (e.g., amide, acetyl, propionyl, and a 3 to 20 carbon alkyl, etc.) coupled to the amino or carboxyl terminus. In certain embodiments, the protecting group coupled to the carboxyl terminus is an amide. In certain embodiments, the protecting group coupled to the amino terminus is an acetyl, a propeonyl, or a 3 to 20 carbon alkyl. Certain peptides comprise both a carboxyl- and an amino-terminus protecting group. In one such embodiment, the amino terminus protecting group is a protecting group selected from the group consisting of acetyl, propionyl, and a 3 to 20 carbon alkyl; and the carboxyl terminal protecting group is an amide.

In certain embodiments, the peptide is one that protects a phospholipid against oxidation by an oxidizing agent selected from the group consisting of hydrogen peroxide, 13(S)-HPODE, 15(S)-HPETE, HPODE, HPETE, HODE, and HETE. The phospholipid can be a phospholipid selected from the group consisting of 1-palmitoyl-2-arachidonoyl-sn-glycero-3-phosphorylcholine (Ox-PAPC), 1-palmitoyl-2-oxovaleroyl-sn-glycero-3-phosphorylcholine (POVPC), 1-palmitoyl-2-glutaroyl-sn-glycero-3-phosphorylcholine (PGPC), 1-palmitoyl-2-epoxyisoprostane-sn-glycero-3-phosphorylcholine (PEIPC), 1-stearoyl-2-arachidonoyl-sn-glycero-3-phosphorylcholine (SAPC), 1-stearoyl-2-oxovaleroyl-sn-glycero-3-phosphorylcholine (SOVPC), 1-stearoyl-2-glutaroyl-sn-glycero-3-phosphorylcholine (SGPC), 1-stearoyl-2-epoxyisoprostane-sn-glycero-3-phosphorylcholine (SEIPC), 1-stearoyl-2-arachidonyl-sn-glycero-3-phosphorylethanolamine (Ox-SAPE), 1-stearoyl-2-oxovaleroyl-sn-glycero-3-phosphorylethanolamine (SOVPE), 1-stearoyl-2-glutaroyl-sn-glycero-3-phosphorylethanolamine (SGPE), and 1-stearoyl-2-epoxyisoprostane-sn-glycero-3-phosphorylethanolamine (SEI PE).

In another embodiment, this invention provides a composition, suitable for oral administration, that ameliorates a symptom of atherosclerosis. The composition comprises a peptide that is a human apo A-I peptide or fragment thereof comprising a class A amphipathic helix, or an analogue of a human apo A-I peptide wherein said peptide has a first protecting group attached to an amino terminal and a second protecting group attached to a carboxyl terminal and further wherein said peptide comprises a plurality of D amino acid residues. The protecting groups include, but are not limited to the protecting groups described herein. In certain embodiments, more than half, more preferably more than 80%, and most preferably more than 90% or even all of the enantiomeric amino acids comprising the peptide are D amino acids. The composition can further comprise a pharmaceutically acceptable excipient (e.g., an excipient suitable for oral administration or an excipient suitable for injection). Preferred peptides are capable of protecting a phospholipid (e.g., 1-palmitoyl-2-arachidonoyl-sn-glycero-3-phosphorylcholine (Ox-PAPC), 1-palmitoyl-2-oxovaleroyl-sn-glycero-3-phosphorylcholine (POVPC), 1-palmitoyl-2-glutaroyl-sn-glycero-3-phosphorylcholine (PGPC), 1-palmitoyl-2-epoxyisoprostane-sn-glycero-3-phosphorylcholine (PEIPC), 1-stearoyl-2-arachidonoyl-sn-glycero-3-phosphorylcholine (SAPC), 1-stearoyl-2-oxovaleroyl-sn-glycero-3-phosphorylcholine (SOVPC), 1-stearoyl-2-glutaroyl-sn-glycero-3-phosphorylcholine (SGPC), 1-stearoyl-2-epoxyisoprostane-sn-glycero-3-phosphorylcholine (SEIPC), 1-stearoyl-2-arachidonyl-sn-glycero-3-phosphorylethanolaamine (Ox-SAPE), 1-stearoyl-2-oxovaleroyl-sn-glycero-3-phosphorylethanolamine (SOVPE), 1-stearoyl-2-glutaroyl-sn-glycero-3-phosphorylethanolamine (SGPE), and 1-stearoyl-2-epoxyisoprostane-sn-glycero-3-phosphorylethanolamine (SEI PE), etc.) from oxidization by an oxidizing agent (e.g. hydrogen peroxide, 13(S)-HPODE, 15(S)-HPETE, HPODE, HPETE, HODE, and HETE).

This invention also provides methods of ameliorating a symptom of atherosclerosis. The methods comprise administering to an organism (e.g. human or non-human mammal) one or more of the peptides described herein. In particularly preferred embodiments, such peptides comprise a plurality of "D" amino acids and/or are protected as described herein. The peptide is preferably orally administered to the organism and the organism is preferably an organism diagnosed as having or as at risk for one or more symptoms of atherosclerosis. In certain embodiments, the peptide can be provided as an isolated peptide or combined with a pharmacological excipient as described herein. The administration is preferably at a dosage sufficient to ameliorate one or more symptoms of atherosclerosis and/or to significantly reduce the likelihood of occurrence of one or more symptoms of atherosclerosis.

In still another embodiment, this invention provides a kit for ameliorating a symptom of atherosclerosis. Preferred kits include a container containing one or more of the peptides described herein. The peptides preferably comprise a plurality of "D" amino acids and/or are protected as described herein. In certain embodiments, the kit can optionally further include a pharmaceutically acceptable excipient and/or the peptide is provided combined with a with a pharmaceutically acceptable excipient (e.g. in a unit dosage formulation). Preferred kits provided the peptide(s) as a unit dosage formulation is for oral administration. The kits also, optionally, include instructional materials teaching the use of said peptide for ameliorating one or more symptoms of atherosclerosis and/or for reducing the likelihood of occurrence of one or more symptoms of atherosclerosis.

In certain embodiments, this invention excludes any one or more peptides disclosed in U.S. Pat. No. 3,767,040 and/or in Garber et al. (1992) *Arteriosclerosis and Thrombosis*, 12: 886–894. In preferred embodiments, this invention excludes peptides having the formula $A_1$-$B_1$-$B_2$-$C_1$-D-$B_3$-$B_4$-$A_2$-$C_2$-$B_5$-$B_6$-$A_3$-$C_3$-$B_7$-$C_4$-$A_4$-$B_8$-$B_9$ where $A_1$, $A_2$, $A_3$ and $A_4$ are independently aspartic acid or glutamic acid, or homologues or analogues thereof; $B_1$, $B_2$, $B_3$, $B_4$, $B_5$, $B_6$, $B_7$, $B_8$ and $B_9$ are independently tryptophan, phenylalanine, alanine, leucine, tyrosine, isoleucine, valine or α-naphthylalanine, or homologues or analogues thereof; $C_1$, $C_2$, $C_3$ and $C_4$ are independently lysine or arginine, and D is serine, threonine, alanine, glycine, histidine, or homologues or analogues thereof; provided that, when $A_1$ and $A_2$ are aspartic acid, $A_3$ and $A_4$ are glutamic acid, $B_2$ and $B_9$ are leucine, $B_3$ and $B_7$ are phenylalanine, $B_4$ is tyrosine, $B_5$ is valine, $B_6$, $B_8$, and D are alanine, and $C_1$, $C_2$, $C_3$ and $C_4$ are lysine, $B_1$ is not tryptophan.

Definitions

The terms "polypeptide", "peptide" and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers.

The term "class A amphipathic helix" refers to a protein structure that forms an α-helix producing a segregation of a polar and nonpolar faces with the positively charged residues residing at the polar-nonpolar interface and the negatively charged residues residing at the center of the polar face (see, e.g., "Segrest et al. (1990) *Proteins: Structure, Function, and Genetics* 8: 103–117).

The term "ameliorating" when used with respect to "ameliorating one or more symptoms of atherosclerosis" refers to a reduction, prevention, or elimination of one or more symptoms characteristic of atherosclerosis and/or associated pathologies. Such a reduction includes, but is not limited to a reduction or elimination of oxidized phospholipids, a reduction in atherosclerotic plaque formation and rupture, a reduction in clinical events such as heart attack, angina, or stroke, a decrease in hypertension, a decrease in inflammatory protein biosynthesis, reduction in plasma cholesterol, and the like.

The term "enantiomeric amino acids" refers to amino acids that can exist in at least two forms that are nonsuperimposable mirror images of each other. Most amino acids (except glycine) are enantiomeric and exist in a so-called L-form (L amino acid) or D-form (D amino acid). Most naturally occurring amino acids are "L" amino acids. The terms "D amino acid" and "L amino acid" are used to refer to absolute configuration of the amino acid, rather than a particular direction of rotation of plane-polarized light. The usage herein is consistent with standard usage by those of skill in the art.

The term "protecting group" refers to a chemical group that, when attached to a functional group in an amino acid (e.g. a side chain, an alpha amino group, an alpha carboxyl group, etc.) blocks or masks the properties of that functional group. Amino protecting groups include, but are not limited to acetyl, or amino groups. Other amino protecting groups include, but are not limited to alkyl chains as in fatty acids, propionyl, formyl and others. Preferred carboxyl protecting groups include, but are not limited to groups that form amides or esters.

The phrase "protect a phospholipid from oxidation by an oxidizing agent" refers to the ability of a compound to reduce the rate of oxidation of a phospholipid (or the amount of oxidized phospholipid produced) when that phospholipid is contacted with an oxidizing agent (e.g. hydrogen peroxide, 13(S)-HPODE, 15(S)-BPETE, HPODE, HPETE, HODE, HETE, etc.).

The terms "low density lipoprotein" or "LDL" is defined in accordance with common usage of those of skill in the art. Generally, LDL refers to the lipid-protein complex which when isolated by ultracentrifugation is found in the density range d=1.019 to d=1.063.

The terms "high density lipoprotein" or "HDL" is defined in accordance with common usage of those of skill in the art. Generally "HDL" refers to a lipid-protein complex which when isolated by ultracentrifugation is found in the density range of d=1.063 to d=1.21.

The term "Group I HDL" refers to a high density lipoprotein or components thereof (e.g. apo A-I, paraoxonase, platelet activating factor acetylhydrolase, etc.) that reduce oxidized lipids (e.g. in low density lipoproteins) or that protect oxidized lipids from oxidation by oxidizing agents.

The term "Group II HDL" refers to an HDL that offers reduced activity or no activity in protecting lipids from oxidation or in repairing (e.g. reducing) oxidized lipids.

The term "HDL component" refers to a component (e.g. molecules) that comprises a high density lipoprotein (HDL). Assays for HDL that protect lipids from oxidation or that repair (e.g. reduce oxidized lipids) also include assays for components of HDL (e.g. apo A-I, paraoxonase, platelet activating factor acetylhydrolase, etc.) that display such activity.

The term "human apo A-I peptide" refers to a full-length human apo A-I peptide or to a fragment or domain thereof comprising a class A amphipathic helix.

A "monocytic reaction" as used herein refers to monocyte activity characteristic of the "inflammatory response" associated with atherosclerotic plaque formation. The monocytic reaction is characterized by monocyte adhesion to cells of the vascular wall (e.g. cells of the vascular endothelium), and/or chemotaxis into the subendothelial space, and/or differentiation of monocytes into macrophages.

The term "absence of change" when referring to the amount of oxidized phospholipid refers to the lack of a detectable change, more preferably the lack of a statistically significant change (e.g. at least at the 85%, preferably at least at the 90%, more preferably at least at the 95%, and most preferably at least at the 98% or 99% confidence level). The absence of a detectable change can also refer to assays in which oxidized phospholipid level changes, but not as much as in the absence of the protein(s) described herein or with reference to other positive or negative controls.

The following abbreviations are used herein: PAPC: L-α-1-palmitoyl-2-arachidonoyl-sn-glycero-3-phosphocholine;

POVPC: 1-palmitoyl-2-(5-oxovaleryl)-sn-glycero-3-phosphocholine; PGPC: 1-palmitoyl-2-glutaryl-sn-glycero-3-phosphocholine; PEIPC: 1-palmitoyl-2-(5,6-epoxyisoprostane $E_2$)-sn-glycero-3-phsophocholine; ChC18:2: cholesteryl linoleate; ChC18:2-OOH: cholesteryl linoleate hydroperoxide; DMPC: 1,2-ditetradecanoyl-rac-glycerol-3-phosphocholine; PON: paraoxonase; HPF: Standardized high power field; PAPC: L-α-1-palmitoyl-2-arachidonoyl-sn-glycero-3-phosphocholine; POVPC: 1-palmitoyl-2-(5-oxovaleryl)-sn-glycero-3-phosphocholine; PGPC: 1-palmitoyl-2-glutaryl-sn-glycero-3-phosphocholine; PEIPC: 1-palmitoyl-2-(5,6-epoxyisoprostane $E_2$)-sn-glycero-3-phosphocholine; PON: paraoxonase; HPF: Standardized high power field; BL/6: C57BL/6J; C3H:C3H/HeJ.

The term "conservative substitution" is used in reference to proteins or peptides to reflect amino acid substitutions that do not substantially alter the activity (specificity or binding affinity) of the molecule. Typically conservative amino acid substitutions involve substitution one amino acid for another amino acid with similar chemical properties (e.g. charge or hydrophobicity). The following six groups each contain amino acids that are typical conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W).

The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection. With respect to the peptides of this invention sequence identity is determined over the full length of the peptide.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman (1988) *Proc. Natl. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle (1987) *J. Mol. Evol.* 35:351–360. The method used is similar to the method described by Higgins & Sharp (1989) *CABIOS* 5: 151–153. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described in Altschul et al. (1990) *J. Mol. Biol.* 215: 403–410. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul (1993) *Proc. Natl. Acad. Sci. USA*, 90: 5873–5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

The term "D-18A peptide" refers to a peptide having the sequence: D-W-L-K-A-F-Y-D-K-V-A-E-K-L-K-E-A-F (SEQ ID NO: 1) where all of the enantiomeric amino acids are D form amino acids.

DETAILED DESCRIPTION

Figure 1A:
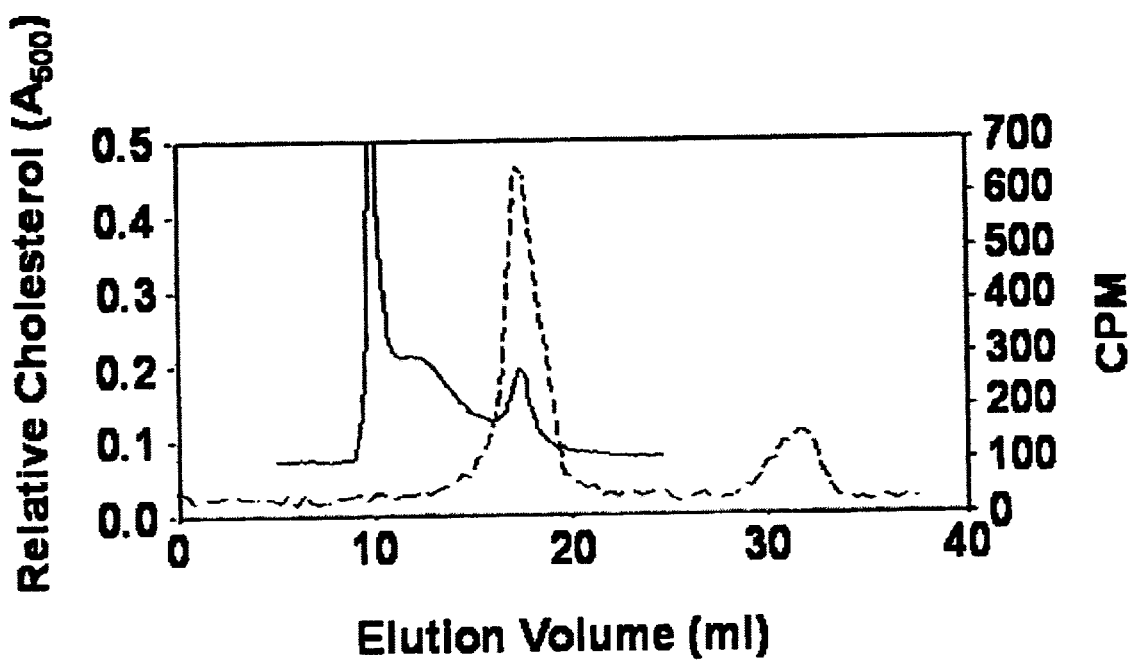
FIG. 1 illustrates the plasma distributions of peptide 5F or apo A-I following intraperitoneal injection. Human apo A-I, mouse apo A-I, and peptide 5F were labeled with $^{125}$I and injected intraperitoneally into C57BL/6 mice that had been fed the atherogenic diet for at least three weeks. Samples were taken during the kinetic studies described in Table 2. Representative samples were analyzed by the CLiP method, and fractions were collected for determination of radioactivity. The elution volume was based on the column pump rate only; the volume contributed by the enzymatic reagent pump was neglected. Data shown are cholesterol (as absorbance at 500 nm in arbitrary units; solid lines) and radioactivity (in counts per minute; dashed lines). Panels are A: human apo A-I (one hour following injection); B: mouse apo A-I (one hour), C: 5F (1.5 hours).

I. Mitigation of a Symptom of Atherosclerosis

This invention pertains to the discovery that synthetic peptides designed to mimic the class A amphipathic helical motif (Segrest et al. (1990) *Proteins: Structure, Function, and Genetics* 8: 103–117) are able to associate with phospholipids and exhibit many biological properties similar to human apo-A-I. In particular, it was a discovery of this invention that when such peptides are formulated using D amino acids, the peptides show dramatically elevated serum half-lives and, particularly when the amino and/or carboxy termini are blocked, can even be orally administered.

Moreover, it was a surprising discovery of this invention that such D-form peptides retain the biological activity of the corresponding L-form peptide. In vivo animal studies using such D-form peptides showed effective oral delivery, elevated serum half-life, and the ability to mitigate or prevent/inhibit one or more symptoms of atherosclerosis.

We discovered that normal HDL inhibits three steps in the formation of mildly oxidized LDL. In those studies (see, copending application U.S. Ser. No. 09/541,468, filed on Mar. 31, 2000) we demonstrated that treating human LDL in vitro with apo A-I or an apo A-I mimetic peptide (37pA) removed seeding molecules from the LDL that included HPODE and HPETE. These seeding molecules were required for cocultures of human artery wall cells to be able to oxidize LDL and for the LDL to induce the artery wall cells to produce monocyte chemotactic activity. We also demonstrated that after injection of apo A-I into mice or infusion into humans, the LDL isolated from the mice or human volunteers after injection/infusion of apo A-I was resistant to oxidation by human artery wall cells and did not induce monocyte chemotactic activity in the artery wall cell cocultures.

It is demonstrated herein, that HDL from mice that were fed an atherogenic diet and injected with PBS failed to inhibit the oxidation of human LDL and failed to inhibit LDL-induced monocyte chemotactic activity in human artery wall cocultures. In contrast, HDL from mice fed an atherogenic diet and injected daily with peptides described herein was as effective in inhibiting human LDL oxidation and preventing LDL-induced monocyte chemotactic activity in the cocultures as was normal human HDL. In addition, LDL taken from mice fed the atherogenic diet and injected daily with PBS was more readily oxidized and more readily induced monocyte chemotactic activity than LDL taken from mice fed the same diet but injected with 20 µg daily of peptide 5F.

The in vitro responses of human artery wall cells to HDL and LDL from mice fed the atherogenic diet and injected with a peptide according to this invention are consistent with the protective action of shown by such peptides in vivo. Despite, similar levels of total cholesterol, LDL-cholesterol, IDL+VLDL-cholesterol, and lower HDL-cholesterol as a percent of total cholesterol, the animals fed the atherogenic diet and injected with the peptide had significantly lower lesion scores. The peptides of this invention thus prevented progression of atherosclerotic lesions in mice fed an atherogenic diet.

Thus, in one embodiment, this invention provides methods for ameliorating and/or preventing one or more symptoms of atherosclerosis. The methods preferably involve administering to an organism, preferably a mammal, more preferably a human one or more of the peptides of this invention (or mimetics of such peptides). The peptide(s) can be administered, as described herein, according to any of a number of standard methods including, but not limited to injection, suppository, nasal spray, time-release implant, transdermal patch, and the like. In one particularly preferred embodiment, the peptide(s) are administered orally (e.g. as a syrup, capsule, or tablet).

The methods involve the administration of a single polypeptide of this invention or the administration of two or more different polypeptides. The polypeptides can be provided as monomers or in dimeric, oligomeric or polymeric forms. In certain embodiments, the multimeric forms may comprise associated monomers (e.g. ionically or hydrophobically linked) while certain other multimeric forms comprise covalently linked monomers (directly linked or through a linker).

While the invention is described with respect to use in humans, it is also suitable for animal, e.g. veterinary use. Thus preferred organisms include, but are not limited to humans, non-human primates, canines, equines, felines, porcines, ungulates, largomorphs, and the like.

The methods of this invention are not limited to humans or non-human animals showing one or more symptom(s) of atherosclerosis (e.g. hypertension, plaque formation and rupture, reduction in clinical events such as heart attack, angina, or stroke, high levels of plasma cholesterol, high levels of low density lipoprotein, high levels of very low density lipoprotein, or inflammatory proteins, etc.), but are useful in a prophylactic context. Thus, the peptides of this invention (or mimetics thereof) may be administered to organisms to prevent the onset/development of one or more symptoms of atherosclerosis. Particularly preferred subjects in this context are subjects showing one or more risk factors for atherosclerosis (e.g. family history, hypertension, obesity, high alcohol consumption, smoking, high blood cholesterol, high blood triglycerides, elevated blood LDL, VLDL, IDL, or low HDL, diabetes, or a family history of diabetes, high blood lipids, heart attack, angina or stroke, etc.).

In addition to methods of use of the atherosclerosis-inhibiting peptides of this invention, this invention also provides the peptides themselves, the peptides formulated as pharmaceuticals, particularly for oral delivery, and kits for the treatment and/or prevention of one or more symptoms of atherosclerosis.

II. Preferred Peptides and Their Preparation

Preferred Peptides.

It was a discovery of this invention that class A peptides, are capable of mitigating one or more symptoms of atherosclerosis. Class A peptides are characterized by formation of an α-helix that produces a segregation of polar and nonpolar residues thereby forming a polar and a nonpolar face with the positively charged residues residing at the polar-nonpolar interface and the negatively charged residues residing at the center of the polar face (see, e.g., Anantharamaiah (1986) *Meth. Enzymol*, 128: 626–668). It is noted that the fourth exon of apo A-I, when folded into 3.667 residues/turn produces a class A amphipathic helical structure.

One particularly preferred class A peptide, designated 18A (see, Table 1, and also Anantharamaiah (1986) *Meth. Enzymol*, 128: 626–668) was modified as described herein to produce peptides orally administratable and highly effective at inhibiting or preventing one or more symptoms of atherosclerosis. Without being bound by a particular theory, it is believed that the peptides of this invention act in vivo may by picking up seeding molecule(s) that mitigate oxidation of LDL.

We determined that increasing the number of Phe residues on the hydrophobic face of 18A would theoretically increase lipid affinity as determined by the computation described by Palgunachari et al. (1996) *Arteriosclerosis, Thrombosis, & Vascular Biology* 16: 328–338. Theoretically, a systematic substitution of residues in the nonpolar face of 18A with Phe could yield six peptides. Peptides with an additional 2, 3 and 4 Phe would have theoretical lipid affinity ($\lambda$) values of 13, 14 and 15 units, respectively. However, the 1 values jumped four units if the additional Phe were increased from 4 to 5 (to 19$\lambda$ units). Increasing to 6 or 7 Phe would produce a less dramatic increase (to 20 and 21$\lambda$ units, respectively). Therefore, we chose 5 additional Phe (and hence the peptides designation as 5F). In one particularly preferred embodiment, the 5F peptide was blocked in that the amino terminal residue was acetylated and the carboxyl terminal residue was amidated.

The new class A peptide analog, 5F inhibited, lesion development in atherosclerosis-susceptible mice. The new peptide analog, 5F, was compared with mouse apo A-I (MoA-I) for efficacy in inhibiting diet-induced atherosclerosis in these mice using peptide dosages based on the study by Levine et al. (Levine et al. (1993) *Proc. Natl. Acad. Sci. USA* 90:12040–12044).

A number of other class A peptides were also produced and showed varying, but significant degrees of efficacy in mitigating one or more symptoms of atherosclerosis. A number of such peptides are illustrated in Table 1.

TABLE 1

Preferred peptides for use in this invention.

| Peptide Name | Amino Acid Sequence | SEQ ID NO. |
|---|---|---|
| 18A | Asp-Trp-Leu-Lys-Ala-Phe-Tyr-Asp-Lys-Val-Ala-Glu-Lys-Leu-Lys-Glu-Ala-Phe | 1 |
| 2F | Ac-Asp-Trp-Leu-Lys-Ala-Phe-Tyr-Asp-Lys-Val-Ala-Glu-Lys-Leu-Lys-Glu-Ala-Phe-NH$_2$ | 2 |
| 3F | Ac-Asp-Trp-Phe-Lys-Ala-Phe-Tyr-Asp-Lys-Val-Ala-Glu-Lys-Leu-Lys-Glu-Ala-Phe-NH$_2$ | 3 |
| 3F14 | Ac-Asp-Trp-Leu-Lys-Ala-Phe-Tyr-Asp-Lys-Val-Ala-Glu-Lys-Phe-Lys-Glu-Ala-Phe-NH$_2$ | 4 |
| 5F | Ac-Asp-Trp-Phe-Lys-Ala-Phe-Tyr-Asp-Lys-Val-Ala-Glu-Lys-Phe-Lys-Glu-Ala-Phe-NH$_2$ | 5 |
| 6F | Ac-Asp-Trp-Leu-Lys-Ala-Phe-Tyr-Asp-Lys-Phe-Phe-Glu-Lys-Phe-Lys-Glu-Phe-Phe-NH$_2$ | 6 |
| 7F | Ac-Asp-Trp-Phe-Lys-Ala-Phe-Tyr-Asp-Lys-Phe-Phe-Glu-Lys-Phe-Lys-Glu-Phe-Phe-NH$_2$ | 7 |
|  | Ac-Asp-Trp-Leu-Lys-Ala-Phe-Tyr-Asp-Lys-Val-Ala-Glu-Lys-Phe-Lys-Glu-Ala-Phe-NH$_2$ | 8 |
| 7 | Ac-Asp-Trp-Leu-Lys-Ala-Phe-Tyr-Asp-Lys-Val-Ala-Glu-Lys-Leu-Lys-Glu-Phe-Phe-NH$_2$ | 9 |
|  | Ac-Asp-Trp-Leu-Lys-Ala-Phe-Tyr-Asp-Lys-Val-Phe-Glu-Lys-Phe-Lys-Glu-Ala-Phe-NH$_2$ | 10 |
|  | Ac-Asp-Trp-Leu-Lys-Ala-Phe-Tyr-Asp-Lys-Val-Phe-Glu-Lys-Leu-Lys-Glu-Phe-Phe-NH$_2$ | 11 |
|  | Ac-Asp-Trp-Leu-Lys-Ala-Phe-Tyr-Asp-Lys-Val-Ala-Glu-Lys-Phe-Lys-Glu-Phe-Phe-NH$_2$ | 12 |
|  | Ac-Asp-Trp-Leu-Lys-Ala-Phe-Tyr-Asp-Lys-Val-Phe-Glu-Lys-Phe-Lys-Glu-Phe-Phe-NH$_2$ | 13 |
|  | Ac-Glu-W-Leu-Lys-Leu-Phe-Tyr-Glu-Lys-Val-Leu-Glu-Lys-Phe-Lys-Glu-Ala-Phe-NH$_2$ | 14 |
|  | Ac-Glu-W-Leu-Lys-Ala-Phe-Tyr-Asp-Lys-Val-Ala-Glu-Lys-Phe-Lys-Glu-Ala-Phe-NH$_2$ | 15 |
|  | Ac-Glu-W-Leu-Lys-Ala-Phe-Tyr-Asp-Lys-Val-Ala-Glu-Lys-Leu-Lys-Glu-Phe-Phe-NH$_2$ | 16 |
|  | Ac-Glu-W-Leu-Lys-Ala-Phe-Tyr-Asp-Lys-Val-Phe-Glu-Lys-Phe-Lys-Glu-Ala-Phe-NH$_2$ | 17 |
|  | Ac-Glu-W-Leu-Lys-Ala-Phe-Tyr-Asp-Lys-Val-Phe-Glu-Lys-Leu-Lys-Glu-Phe-Phe-NH$_2$ | 18 |
|  | Ac-Glu-W-Leu-Lys-Ala-Phe-Tyr-Asp-Lys-Val-Ala-Glu-Lys-Phe-Lys-Glu-Phe-Phe-NH$_2$ | 19 |
|  | Ac-Glu-W-Leu-Lys-Ala-Phe-Tyr-Asp-Lys-Val-Phe-Glu-Lys-Phe-Lys-Glu-Phe-Phe-NH$_2$ | 20 |
|  | AC-Ala-Phe-Tyr-Asp-Lys-Val-Ala-Glu-Lys-Leu-Lys-Glu-Ala-Phe-NH$_2$ | 21 |
|  | Ac-Ala-Phe-Tyr-Asp-Lys-Val-Ala-Glu-Lys-Phe-Lys-Glu-Ala-Phe-NH$_2$ | 22 |
|  | Ac-Ala-Phe-Tyr-Asp-Lys-Val-Ala-Glu-Lys-Phe-Lys-Glu-Ala-Phe-NH$_2$ | 23 |
|  | Ac-Ala-Phe-Tyr-Asp-Lys-Phe-Phe-Glu-Lys-Phe-Lys-Glu-Phe-Phe-NH$_2$ | 24 |
|  | Ac-Ala-Phe-Tyr-Asp-Lys-Phe-Phe-Glu-Lys-Phe-Lys-Glu-Phe-Phe-NH$_2$ | 25 |
|  | Ac-Ala-Phe-Tyr-Asp-Lys-Val-Ala-Glu-Lys-Phe-Lys-Glu-Ala-Phe-NH$_2$ | 26 |
|  | Ac-Ala-Phe-Tyr-Asp-Lys-Val-Ala-Glu-Lys-Leu-Lys-Glu-Phe-Phe-NH$_2$ | 27 |
|  | Ac-Ala-Phe-Tyr-Asp-Lys-Val-Phe-Glu-Lys-Phe-Lys-Glu-Ala-Phe-NH$_2$ | 28 |
|  | Ac-Ala-Phe-Tyr-Asp-Lys-Val-Phe-Glu-Lys-Leu-Lys-Glu-Phe-Phe-NH$_2$ | 29 |
|  | Ac-Ala-Phe-Tyr-Asp-Lys-Val-Ala-Glu-Lys-Phe-Lys-Glu-Phe-Phe-NH$_2$ | 30 |
|  | Ac-Lys-Ala-Phe-Tyr-Asp-Lys-Val-Phe-Glu-Lys-Phe-Lys-Glu-Phe-Phe-NH$_2$ | 31 |
|  | Ac-Leu-Phe-Tyr-Glu-Lys-Val-Leu-Glu-Lys-Phe-Lys-Glu-Ala-Phe-NH$_2$ | 32 |
|  | Ac-Ala-Phe-Tyr-Asp-Lys-Val-Ala-Glu-Lys-Phe-Lys-Glu-Ala-Phe-NH$_2$ | 33 |
|  | Ac-Ala-Phe-Tyr-Asp-Lys-Val-Ala-Glu-Lys-Leu-Lys-Glu-Phe-Phe-NH$_2$ | 34 |
|  | Ac-Ala-Phe-Tyr-Asp-Lys-Val-Phe-Glu-Lys-Phe-Lys-Glu-Ala-Phe-NH$_2$ | 35 |
|  | Ac-Ala-Phe-Tyr-Asp-Lys-Val-Phe-Glu-Lys-Leu-Lys-Glu-Phe-Phe-NH$_2$ | 36 |
|  | Ac-Ala-Phe-Tyr-Asp-Lys-Val-Ala-Glu-Lys-Phe-Lys-Glu-Phe-Phe-NH$_2$ | 37 |

TABLE 1-continued

Preferred peptides for use in this invention.

| Peptide Name | Amino Acid Sequence | SEQ ID NO. |
|---|---|---|
| | Ac-Ala-Phe-Tyr-Asp-Lys-Val-Phe-Glu-Lys-Phe-Lys-Glu-Phe-Phe-NH$_2$ | 38 |

While the various peptides of Table 1, except 18A, are illustrated with an acetyl group protecting the amino terminus and an amide group protecting the carboxyl terminus, either or both of these protecting groups may be eliminated and/or substituted with another protecting group as described herein. In particularly preferred embodiments, the peptides comprise one or more D-form amino acids as described herein.

It is also noted that Table 1 is not fully inclusive. Using the teaching provided herein, other suitable peptides can routinely be produced (e.g. by conservative or semi-conservative substitutions (e.g. D replaced by E), extensions, deletions, and the like). Thus, for example, one embodiment utilizes truncations of any one or more of peptides identified by SEQ ID Nos: 2–20. Thus, for example, SEQ ID NO: 21 illustrates a peptide comprising 14 amino acids from the c-terminus of 18A comprising one or more D amino acids, while SEQ ID NOS: 22–38 illustrate other truncations. Longer peptides are also suitable. Such longer peptides may entirely form a class A amphipathic helix, or the class A amphipathic helix (helices) may form one or more domains of the peptide. In addition, this invention contemplates multimeric versions of the peptides. Thus, for example, the peptides illustrated in Table 1 can be coupled together (directly or with one or more intervening amino acids). One such polymeric peptide is 18A-Pro-18A, preferably comprising one or more D amino acids as described herein and/or having one or both termini protected.

It was a surprising discovery of this invention that, when the class A peptides (e.g. as illustrated in Table 1) incorporated D amino acids they retained their activity and, but could be administered orally. Moreover this oral administration resulted in relatively efficient uptake and significant serum half-life thereby providing an efficacious method of mitigating one or more symptoms of atherosclerosis.

Using the teaching provided herein, one of skill can routinely modify the illustrated class A peptides to produce other suitable class A peptides of this invention. For example, routine conservative or semi-conservative substitutions (e.g. E for D) can be made of the existing amino acids. The effect of various substitutions on lipid affinity of the resulting peptide can be predicted using the computational method described by Palgunachari et al. (1996) *Arteriosclerosis, Thrombosis, & Vascular Biology* 16: 328–338. The peptides can be lengthened or shortened as long as the class A α-helix structure is preserved. In addition, substitutions can be made to render the resulting peptide more similar to peptide(s) endogenously produced by the subject species.

In certain embodiments, the peptides of this invention comprise "D" forms of the peptides described in U.S. Pat. No. 4,643,988, more preferably "D" forms having one or both termini coupled to protecting groups. Such peptides include peptides having the formula $A_1$-$B_1$-$B_2$-$C_1$-D-$B_3$-$B_4$-$A_2$-$C_2$-$B_5$-$B_6$-$A_3$-$C_3$-$B_7$-$C_4$-$A_4$-$B_8$-$B_9$ wherein $A_1$, $A_2$, $A_3$ and $A_4$ are independently aspartic acid or glutamic acid, or homologues or analogues thereof; $B_1$, $B_2$, $B_3$, $B_4$, $B_5$, $B_6$, $B_7$, $B_8$ and $B_9$ are independently tryptophan, phenylalanine, alanine, leucine, tyrosine, isoleucine, valine or cc-naphthylalanine, or homologues or analogues thereof; $C_1$, $C_2$, $C_3$ and $C_4$ are independently lysine or arginine, and D is serine, threonine, alanine, glycine, histidine, or homologues or analogues thereof; provided that, when $A_1$ and $A_2$ are aspartic acid, $A_3$ and $A_4$ are glutamnic acid, $B_2$ and $B_9$ are leucine, $B_3$ and $B_7$ are phenylalanine, $B_4$ is tyrosine, $B_5$ is valine, $B_6$, $B_8$, and D are alanine, and $C_1$, $C_2$, $C_3$ and $C_4$ are lysine, $B_1$ is not Tryptophan, where at one enantiomeric amino acid is a "D" form amino acids. Preferably at least 50% of the enantiomeric amino acids are "D" form, more preferably at least 80% of the enantiomeric amino acids are "D" form, and most preferably at least 90% or even all of the enantiomeric amino acids are "D" form amino acids.

While, in preferred embodiments, the peptides of this invention utilize naturally-occurring amino acids or D forms of naturally occurring amino acids, substitutions with non-naturally occurring amino acids (e.g., methionine sulfoxide, methionine methylsulfonium, norleucine, episilon-aminocaproic acid, 4-aminobutanoic acid, tetrahydroisoquinoline-3-carboxylic acid, 8-aminocaprylic acid, 4-aminobutyric acid, Lys(N(epsilon)-trifluoroacetyl), α-aminoisobutyric acid, and the like) are also contemplated.

In addition to the class A peptides described herein, peptidomimetics are also contemplated herein. Peptide analogs are commonly used in the pharmaceutical industry as non-peptide drugs with properties analogous to those of the template peptide. These types of non-peptide compound are termed "peptide mimetics" or "peptidomimetics" (Fauchere (1986) *Adv. Drug Res.* 15: 29; Veber and Freidinger (1985) *TINS* p.392; and Evans et al. (1987) *J. Med. Chem.* 30: 1229) and are usually developed with the aid of computerized molecular modeling. Peptide mimetics that are structurally similar to therapeutically useful peptides may be used to produce an equivalent therapeutic or prophylactic effect.

Generally, peptidomimetics are structurally similar to a paradigm polypeptide (i.e., 5F described herein), but have one or more peptide linkages optionally replaced by a linkage selected from the group consisting of: —CH$_2$NH—, —CH$_2$S—, —CH$_2$—CH$_2$—, —CH=CH—(cis and trans), —COCH$_2$—, —CH(OH)CH$_2$—, —CH$_2$SO—, etc. by methods known in the art and further described in the following references: Spatola (1983) p. 267 in *Chemistry and Biochemistry of Amino Acids, Peptides, and Proteins*, B. Weinstein, eds., Marcel Dekker, New York,; Spatola (1983) *Vega Data* 1(3) *Peptide Backbone Modifications*. (general review); Morley (1980) *Trends Pharm Sci* pp. 463–468 (general review); Hudson et al. (1979) *Int J Pept Prot Res* 14:177–185 (—CH$_2$NH—, CH$_2$CH$_2$—); Spatola et al. (1986) *Life Sci* 38:1243–1249 (—CH$_2$—S): Hann, (1982) *J Chem Soc Perkin Trans* I 307–314 (—CH—CH—, cis and trans); Almquist et al. (1980) *J Med Chem.* 23:1392–1398 (—COCH$_2$—); Jennings-White et al.(1982) *Tetrahedron Lett.* 23:2533 (—COCH$_2$—); Szelke, M. et al., European Appln. EP 45665 (1982) CA: 97:39405 (1982) (—CH(OH)

CH2—); Holladay et al. (1983) *Tetrahedron Lett* 24:4401–4404 (—C(OH)CH$_2$—); and Hruby (1982) *Life Sci.*, 31:189–199 (—CH$_2$—S—)).

A particularly preferred non-peptide linkage is —CH$_2$NH—. Such peptide mimetics may have significant advantages over polypeptide embodiments, including, for example: more economical production, greater chemical stability, enhanced pharmacological properties (half-life, absorption, potency, efficacy, etc.), reduced antigenicity, and others.

In addition, circularly permutations of the peptides described herein or constrained peptides (including cyclized peptides) comprising a consensus sequence or a substantially identical consensus sequence variation may be generated by methods known in the art (Rizo and Gierasch (1992) *Ann. Rev. Biochem.* 61: 387); for example, by adding internal cysteine residues capable of forming intramolecular disulfide bridges which cyclize the peptide.

Peptide Preparation.

The peptides used in this invention are chemically synthesized using standard chemical peptide synthesis techniques or, particularly where the peptide does not comprise "D" amino acid residues, are recombinantly expressed. In preferred embodiments the peptides are chemically synthesized by any of a number of fluid or solid phase peptide synthesis techniques known to those of skill in the art. Solid phase synthesis in which the C-terminal amino acid of the sequence is attached to an insoluble support followed by sequential addition of the remaining amino acids in the sequence is a preferred method for the chemical synthesis of the polypeptides of this invention. Techniques for solid phase synthesis are well know to those of skill in the art and are described, for example, by Barany and Merrifield (1963) *Solid-Phase Peptide Synthesis*; pp. 3–284 in The *Peptides: Analysis, Synthesis, Biology. Vol. 2: Special Methods in Peptide Synthesis, Part A.*; Merrifield et al. (1963) *J. Am. Chem. Soc.*, 85: 2149–2156, and Stewart et al. (1984) *Solid Phase Peptide Synthesis*, 2nd ed. Pierce Chem. Co., Rockford, Ill.

In a most preferred embodiment, the peptides are synthesized by the solid phase peptide synthesis procedure using a benzhydrylamine resin (Beckman Bioproducts, 0.59 mmol of NH$_2$/g of resin) as the solid support. The COOH terminal amino acid (e.g., t-butylcarbonyl-Phe) is attached to the solid support through a 4-(oxymethyl)phenacetyl group. This is a more stable linkage than the conventional benzyl ester linkage, yet the finished peptide can still be cleaved by hydrogenation. Transfer hydrogenation using formic acid as the hydrogen donor is used for this purpose. Detailed protocols used for peptide synthesis and analysis of synthesized peptides are describe in a miniprint supplement accompanying Anantharamaiah et al. (1985) *J. Biol. Chem.*, 260(16): 10248–10255.

D-form Amino Acids.

D-amino acids are incorporated at one or more positions in the peptide simply by using a D-form derivatized amino acid residue in the chemical synthesis. D-form residues for solid phase peptide synthesis are commercially available from a number of suppliers (see, e.g., Advanced Chem Tech, Louisville; Nova Biochem, San Diego; Sigma, St Louis; Bachem California Inc., Torrance, etc.). The D-form amino acids can be incorporated at any position in the peptide as desired. Thus, for example, in one embodiment, the peptide can comprise a single D-amino acid, while in other embodiments, the peptide comprises at least two, generally at least three, more generally at least four, most generally at least five, preferably at least six, more preferably at least seven and most preferably at least eight D amino acids. In particularly preferred embodiments, essentially every other (enantiomeric) amino acid is a D-form amino acid. In certain embodiments at least 90%, preferably at least 90%, more preferably at least 95% of the enantiomeric amino acids are D-form amino acids. In one particularly preferred embodiment, essentially every enantiomeric amino acid is a D-form amino acid.

Protecting Groups.

In certain embodiments, the one or more R-groups on the constituent amino acids and/or the terminal amino acids are blocked with a protecting group. Without being bound by a particular theory, it was a discovery of this invention that blockage, particularly of the amino and/or carboxyl termini of the subject peptides of this invention greatly improves oral delivery and significantly increases serum half-life.

A wide number of protecting groups are suitable for this purpose. Such groups include, but are not limited to acetyl, amide, and alkyl groups with acetyl and alkyl groups being particularly preferred for N-terminal protection and amide groups being preferred for carboxyl terminal protection. In certain particularly preferred embodiments, the protecting groups include, but are not limited to alkyl chains as in fatty acids, propionyl, formyl, and others. Particularly preferred carboxyl protecting groups include amides, esters, and ether-forming protecting groups. In one preferred embodiment, an acetyl group is used to protect the amino terminus and an amide group is used to protect the carboxyl terminus. These blocking groups enhance the helix-forming tendencies of the peptides. Certain particularly preferred blocking groups include alkyl groups of various lengths, e.g. groups having the formula: CH$_3$—(CH$_2$)$_n$—CO— where n ranges from about 1 to about 20, preferably from about 1 to about 16 or 18, more preferably from about 3 to about 13, and most preferably from about 3 to about 10.

In certain particularly preferred embodiments, the protecting groups include, but are not limited to alkyl chains as in fatty acids, propionyl, formyl, and others. Particularly preferred carboxyl protecting groups include amides, esters, and ether-forming protecting groups. In one preferred embodiment, an acetyl group is used to protect the amino terminus and an amide group is used to protect the carboxyl terminus. These blocking groups enhance the helix-forming tendencies of the peptides. Certain particularly preferred blocking groups include alkyl groups of various lengths, e.g. groups having the formula: CH$_3$—(CH$_2$)$_n$—CO— where n ranges from about 3 to about 20, preferably from about 3 to about 16, more preferably from about 3 to about 13, and most preferably from about 3 to about 10.

Other protecting groups include, but are not limited to Fmoc, t-butoxycarbonyl (t-BOC), 9-fluoreneacetyl group, 1-fluorenecarboxylic group, 9-fluorenecarboxylic group, 9-fluorenone-1-carboxylic group, benzyloxycarbonyl, Xanthyl (Xan), Trityl (Trt), 4-methyltrityl (Mtt), 4-methoxytrityl (Mmt), 4-methoxy-2,3,6-trimethyl-benzenesulphonyl (Mtr), Mesitylene-2-sulphonyl (Mts), 4,4-dimethoxybenzhydryl (Mbh),Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimethyl-2,6-diaxocyclohexylidene)ethyl (Dde), 2,6-dichlorobenzyl (2,6-DiCl-Bzl), 2-chlorobenzyloxycarbonyl (2-Cl-Z), 2-bromobenzyloxycarbonyl (2-Br-Z), Benzyloxymethyl (Bom), cyclohexyloxy (cHxO),t-butoxymethyl (Bum), t-butoxy (tBuO), t-Butyl (tBu), Acetyl (Ac), and Trifluoroacetyl (TFA).

Protecting/blocking groups are well known to those of skill as are methods of coupling such groups to the appropriate residue(s) comprising the peptides of this invention (see, e.g., Greene et al., (1991) *Protective Groups in Organic Synthesis*, 2nd ed., John Wiley & Sons, Inc. Somerset, N.J. In one preferred embodiment, for example, acetylation is accomplished during the synthesis when the peptide is on the resin using acetic anhydride. Amide protection can be achieved by the selection of a proper resin for the synthesis. During the synthesis of the peptides described herein in the examples, rink amide resin was used. After the completion of the synthesis, the semipermanent protecting groups on acidic bifunctional amino acids such as Asp and Glu and basic amino acid Lys, hydroxyl of Tyr are all simultaneously removed. The peptides released from such a resin using acidic treatment comes out with the n-terminal protected as acetyl and the carboxyl protected as $NH_2$ and with the simultaneous removal of all of the other protecting groups.

III. Pharmaceutical Formulations

In order to carry out the methods of the invention, one or more peptides or peptide mimetics of this invention are administered to an individual diagnosed as having one or more symptoms of atherosclerosis, or as being at risk for atherosclerosis. The peptides or peptide mimetics can be administered in the "native" form or, if desired, in the form of salts, esters, amides, prodrugs, derivatives, and the like, provided the salt, ester, amide, prodrug or derivative is suitable pharmacologically, i.e., effective in the present method. Salts, esters, amides, prodrugs and other derivatives of the active agents may be prepared using standard procedures known to those skilled in the art of synthetic organic chemistry and described, for example, by March (1992) *Advanced Organic Chemistry; Reactions, Mechanisms and Structure*, 4th Ed. N.Y. Wiley-Interscience.

For example, acid addition salts are prepared from the free base using conventional methodology, that typically involves reaction with a suitable acid. Generally, the base form of the drug is dissolved in a polar organic solvent such as methanol or ethanol and the acid is added thereto. The resulting salt either precipitates or may be brought out of solution by addition of a less polar solvent. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethane-sulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Particularly preferred acid addition salts of the active agents herein are halide salts, such as may be prepared using hydrochloric or hydrobromic acids. Conversely, preparation of basic salts of the peptides or mimetics are prepared in a similar manner using a pharmaceutically acceptable base such as sodium hydroxide, potassium hydroxide, ammonium hydroxide, calcium hydroxide, trimethylamine, or the like. Particularly preferred basic salts include alkali metal salts, e.g., the sodium salt, and copper salts.

Preparation of esters typically involves functionalization of hydroxyl and/or carboxyl groups which may be present within the molecular structure of the drug. The esters are typically acyl-substituted derivatives of free alcohol groups, i.e., moieties that are derived from carboxylic acids of the formula RCOOH where R is alkyl, and preferably is lower alkyl. Esters can be reconverted to the free acids, if desired, by using conventional hydrogenolysis or hydrolysis procedures.

Amides and prodrugs may also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine. Prodrugs are typically prepared by covalent attachment of a moiety which results in a compound that is therapeutically inactive until modified by an individual's metabolic system.

The peptides or mimetics identified herein are useful for parenteral, topical, oral, or local administration, such as by aerosol or transdermally, for prophylactic and/or therapeutic treatment of atherosclerosis and/or symptoms thereof. The pharmaceutical compositions can be administered in a variety of unit dosage forms depending upon the method of administration. Suitable unit dosage forms, include, but are not limited to powders, tablets, pills, capsules, lozenges, suppositories, patches, nasal sprays, injectibles, implantable sustained-release formulations, etc.

The peptides and/or peptide mimetics of this invention are typically combined with a pharmaceutically acceptable carrier (excipient) to form a pharmacological composition. Pharmaceutically acceptable carriers can contain one or more physiologically acceptable compound(s) that act, for example, to stabilize the composition or to increase or decrease the absorption of the active agent(s). Physiologically acceptable compounds can include, for example, carbohydrates, such as glucose, sucrose, or dextrans, antioxidants, such as ascorbic acid or glutathione, chelating agents, low molecular weight proteins, compositions that reduce the clearance or hydrolysis of the active agents, or excipients or other stabilizers and/or buffers.

Other physiologically acceptable compounds include wetting agents, emulsifying agents, dispersing agents or preservatives which are particularly useful for preventing the growth or action of microorganisms. Various preservatives are well known and include, for example, phenol and ascorbic acid. One skilled in the art would appreciate that the choice of pharmaceutically acceptable carrier(s), including a physiologically acceptable compound depends, for example, on the route of administration of the active agent(s) and on the particular physio-chemical characteristics of the active agent(s).

The excipients are preferably sterile and generally free of undesirable matter. These compositions may be sterilized by conventional, well known sterilization techniques.

In therapeutic applications, the compositions of this invention are administered to a patient suffering from one or more symptoms of atherosclerosis or at risk for atherosclerosis in an amount sufficient to cure or at least partially prevent or arrest the disease and/or its complications. An amount adequate to accomplish this is defined as a "therapeutically effective dose." Amounts effective for this use will depend upon the severity of the disease and the general state of the patient's health. Single or multiple administrations of the compositions may be administered depending on the dosage and frequency as required and tolerated by the patient. In any event, the composition should provide a sufficient quantity of the active agents of the formulations of this invention to effectively treat (ameliorate one or more symptoms) the patient.

The concentration of peptide or mimetic can vary widely, and will be selected primarily based on fluid volumes, viscosities, body weight and the like in accordance with the particular mode of administration selected and the patient's needs. Concentrations, however, will typically be selected to provide dosages ranging from about 0.1 or 1 mg/kg/day to about 50 mg/kg/day and sometimes higher. Typical dosages range from about 3 mg/kg/day to about 3.5 mg/kg/day, preferably from about 3.5 mg/kg/day to about 7.2 mg/kg/day, more preferably from about 7.2 mg/kg/day to about 11.0 mg/kg/day, and most preferably from about 11.0 mg/kg/day to about 15.0 mg/kg/day. It will be appreciated that such dosages may be varied to optimize a therapeutic regimen in a particular subject or group of subjects.

In certain preferred embodiments, the peptides or peptide mimetics of this invention are administered orally (e.g. via a tablet) or as an injectable in accordance with standard methods well known to those of skill in the art. In other preferred embodiments, the peptides, may also be delivered through the skin using conventional transdermal drug delivery systems, i.e., transdermal "patches" wherein the active agent(s) are typically contained within a laminated structure that serves as a drug delivery device to be affixed to the skin. In such a structure, the drug composition is typically contained in a layer, or "reservoir," underlying an upper backing layer. It will be appreciated that the term "reservoir" in this context refers to a quantity of "active ingredient(s)" that is ultimately available for delivery to the surface of the skin. Thus, for example, the "reservoir" may include the active ingredient(s) in an adhesive on a backing layer of the patch, or in any of a variety of different matrix formulations known to those of skill in the art. The patch may contain a single reservoir, or it may contain multiple reservoirs.

In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form. The backing layer in these laminates, which serves as the upper surface of the device, preferably functions as a primary structural element of the "patch" and provides the device with much of its flexibility. The material selected for the backing layer is preferably substantially impermeable to the active agent(s) and any other materials that are present.

Other preferred formulations for topical drug delivery include, but are not limited to, ointments and creams. Ointments are semisolid preparations which are typically based on petrolatum or other petroleum derivatives. Creams containing the selected active agent, are typically viscous liquid or semisolid emulsions, often either oil-in-water or water-in-oil. Cream bases are typically water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. The specific ointment or cream base to be used, as will be appreciated by those skilled in the art, is one that will provide for optimum drug delivery. As with other carriers or vehicles, an ointment base should be inert, stable, nonirritating and nonsensitizing.

Unlike typical peptide formulations, the peptides of this invention comprising D-form amino acids can be administered, even orally, without protection against proteolysis by stomach acid, etc. Nevertheless, in certain embodiments, peptide delivery can be enhanced by the use of protective excipients. This is typically accomplished either by complexing the polypeptide with a composition to render it resistant to acidic and enzymatic hydrolysis or by packaging the polypeptide in an appropriately resistant carrier such as a liposome. Means of protecting polypeptides for oral delivery are well known in the art (see, e.g., U.S. Pat. No. 5,391,377 describing lipid compositions for oral delivery of therapeutic agents).

Elevated serum half-life can be maintained by the use of sustained-release protein "packaging" systems. Such sustained release systems are well known to those of skill in the art. In one preferred embodiment, the ProLease biodegradable microsphere delivery system for proteins and peptides (Tracy (1998) *Biotechnol. Prog.* 14: 108; Johnson et al. (1996), *Nature Med.* 2: 795; Herbert et al. (1998), *Pharmaceut. Res.* 15, 357) a dry powder composed of biodegradable polymeric microspheres containing the protein in a polymer matrix that can be compounded as a dry formulation with or without other agents.

The ProLease microsphere fabrication process was specifically designed to achieve a high protein encapsulation efficiency while maintaining protein integrity. The process consists of (i) preparation of freeze-dried protein particles from bulk protein by spray freeze-drying the drug solution with stabilizing excipients, (ii) preparation of a drug-polymer suspension followed by sonication or homogenization to reduce the drug particle size, (iii) production of frozen drug-polymer microspheres by atomization into liquid nitrogen, (iv) extraction of the polymer solvent with ethanol, and (v) filtration and vacuum drying to produce the final dry-powder product. The resulting powder contains the solid form of the protein, which is homogeneously and rigidly dispersed within porous polymer particles. The polymer most commonly used in the process, poly(lactide-co-glycolide) (PLG), is both biocompatible and biodegradable.

Encapsulation can be achieved at low temperatures (e.g., $-40°$ C.). During encapsulation, the protein is maintained in the solid state in the absence of water, thus minimizing water-induced conformational mobility of the protein, preventing protein degradation reactions that include water as a reactant, and avoiding organic-aqueous interfaces where proteins may undergo denaturation. A preferred process uses solvents in which most proteins are insoluble, thus yielding high encapsulation efficiencies (e.g., greater than 95%).

In another embodiment, one or more components of the solution can be provided as a "concentrate", e.g., in a storage container (e.g., in a premeasured volume) ready for dilution, or in a soluble capsule ready for addition to a volume of water.

The foregoing formulations and administration methods are intended to be illustrative and not limiting. It will be appreciated that, using the teaching provided herein, other suitable formulations and modes of administration can be readily devised.

IV. Additional Pharmacologically Active Agents

Additional pharmacologically active agents may be delivered along with the primary active agents, e.g., the peptides of this invention. In one embodiment, such agents include, but are not limited to agents that reduce the risk of atherosclerotic events and/or complications thereof. Such agents include, but are not limited to beta blockers, beta blockers and thiazide diuretic combinations, statins, aspirin, ace inhibitors, ace receptor inhibitors (ARBs), and the like.

Suitable beta blockers include, but are not limited to cardioselective (selective beta 1 blockers), e.g., acebutolol (Sectral™), atenolol (Tenormin™), betaxolol (Kerlone™), bisoprolol (Zebeta™), metoprolol (Lopressor™), and the like. Suitable non-selective blockers (block beta 1 and beta 2 equally) include, but are not limited to carteolol (Cartrol™), nadolol (Corgard™), penbutolol (Levatol™), pindolol (Visken™), propranolol (Inderal™), timolol (Blockadren™), labetalol (Normodyne™, Trandate™), and the like.

Suitable beta blocker thiazide diuretic combinations include, but are not limited to Lopressor HCT, ZIAC, Tenoretic, Corzide, Timolide, Inderal LA 40/25, Inderide, Normozide, and the like.

Suitable statins include, but are not limited to pravastatin (Pravachol/Bristol-Myers Squibb), simvastatin (Zocor/Merck), lovastatin (Mevacor/Merck), and the like.

Suitable ace inhibitors include, but are not limited to captopril (e.g. Capoten™ by Squibb), benazepril (e.g., Lotensin™ by Novartis), enalapril (e.g., Vasotec™ by Merck), fosinopril (e.g., Monopril™ by Bristol-Myers), lisinopril (e.g. Prinivil™ by Merck or Zestril™ by Astra-Zeneca), quinapril (e.g. Accupril™ by Parke-Davis), ramipril (e.g., Altace™ by Hoechst Marion Roussel, King Pharmaceuticals), imidapril, perindopril erbumine (e.g., Aceon™ by Rhone-Polenc Rorer), trandolapril (e.g., Mavik™ by Knoll Pharmaceutical), and the like. Suitable ARBS (Ace Receptor Blockers) include but are not limited to losartan (e.g. Cozaar™ by Merck), irbesartan (e.g., Avapro™ by Sanofi), candesartan (e.g., Atacand™ by Astra Merck), valsartan (e.g., Diovan™ by Novartis), and the like.

IV. Kits for the Amelioration of One or More Symptoms of Atherosclerosis

In another embodiment this invention provides kits for amelioration of one or more symptoms of atherosclerosis or for the prophylactic treatment of a subject (human or animal) at risk for atherosclerosis. The kits preferably comprise a container containing one or more of the peptides or peptide mimetics of this invention. The peptide or peptide mimetic may be provided in a unit dosage formulation (e.g. suppository, tablet, caplet, patch, etc.) and/or may be optionally combined with one or more pharmaceutically acceptable excipients.

The kit can, optionally, further comprise one or more other agents used in the treatment of heart disease and/or atherosclerosis. Such agents include, but are not limited to, beta blockers, vasodilators, aspirin, statins, ace inhibitors or ace receptor inhibitors (ARBs) and the like, e.g. as described above.

In addition, the kits optionally include labeling and/or instructional materials providing directions (i.e., protocols) for the practice of the methods or use of the "therapeutics" or "prophylactics" of this invention. Preferred instructional materials describe the use of one or more polypeptides of this invention to mitigate one or more symptoms of atherosclerosis and/or to prevent the onset or increase of one or more of such symptoms in an individual at risk for atherosclerosis. The instructional materials may also, optionally, teach preferred dosages/therapeutic regiment, counter indications and the like.

While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

Several synthetic class A peptide analogs have been shown to mimic many of the properties of human apo A-I in vitro. In this example, a new peptide (5F) with increased amphipathicity, was given by intraperitoneal injection, 20 μg/daily, for 16 weeks to C57BL/6J mice fed an atherogenic diet. Mouse apo A-I (MoAI) (50 μg/daily) or phosphate buffer saline (PBS) injections were given to other mice as controls. Total plasma cholesterol levels and lipoprotein profiles were not significantly different among the treated group and the control groups except that the mice receiving 5F or MoAI had lower high density lipoprotein (HDL)-cholesterol when calculated as a percent of total cholesterol. No toxicity or production of antibodies to the injected materials was observed. When LDL was taken from animals injected with 5F and presented to human artery wall cells in vitro it produced less lipid hydrodroperoxides and less LDL-induced chemotactic activity than LDL taken from controls. Additionally, when HDL was taken from mice injected with 5F and presented to human artery wall cells in vitro together with human LDL, there were substantially less lipid hydroperoxides formed and substantially less LDL-induced monocyte chemotactic activity. Mice receiving peptide 5F had significantly less aortic atherosclerotic lesion area compared to mice receiving PBS. Lesion area in mice receiving MoAI was similar to that of the PBS-injected animals. We conclude that 5F may have potential in the prevention and treatment of atherosclerosis.

Materials and Methods

Peptides

Peptide 5F (Ac-18A[Asp Trp Leu Lys Ala Phe Tyr Asp Lys Val Phe Glu Lys Phe Lys Glu Phe Phe]-NH$_2$, SEQ ID NO:13) was synthesized by solid-phase peptide synthesis (Segrest et al. (1990) *Proteins: Structure, Function, and Genetics*, 8: 103–117). The purity of the synthetic peptide was established by analytical HPLC and ion-spray mass spectrometry. The peptide was dialyzed against distilled water and lyophilized before using.

MoAI was isolated from the plasma of C57BL/6J mice (EDTA plasma was purchased from Harlan Bioproducts for Science, Indianapolis, Ind.). MoAI was isolated using a combination of size-exclusion and reversed-phase column chromatography. Briefly, plasma density was adjusted to 1.21 g/ml by addition of KBr, and centrifuged at 50,000 rpm for 24 hours at 4° C. (Ti70 rotor; Beckman, Fullerton, Calif.). The top fraction was collected, dialyzed against water to remove KBr, lyophilized, and delipidated. The pellet was dissolved in Gn:DTT:Tris solution (3 M guanidine HCl, 1 mM dithiothreitol, and 10 mM Tris; pH=8.0), then dialyzed against the same solution using 12,000 MW-cutoff dialysis tubing in order to remove much of the apo A-II and C apolipoproteins from the sample. The sample was then dialyzed against water and lyophilized. The pellet was dissolved in fresh Gn:DTT:Tris solution, and proteins were separated by size-exclusion column chromatography, using an XK26/100 column (2.6×100 cm) packed with bulk-phase Superose 12 (Pharmacia Biotech, Piscataway, N.J.) equilibrated with Gn:DTT:Tris solution. The flow rate was 0.5 ml/min, and 2.5 ml fractions were collected. Fractions corresponding to the apo A-I peak were analyzed by SDS-PAGE, and further purified by preparative C-18 reverse-phase HPLC (Anantharamaiah and Garber (1996) *Meth. Enzymol.* 263: 267–282).

Mice—

All experiments were performed using female C57BL/6J mice (Jackson Laboratory, Bar Harbor, Me.). Mice were purchased at six weeks of age, and the diet studies were begun with mice at eight weeks of age. Mice weighing 20 to 22 grams were used in the turnover studies. All animal studies were prospectively reviewed and approved by the Institutional Animal Care and Use Committee of the University of Alabama at Birmingham.

Kinetic Studies—

The 5F peptide, MoAI, and human apo A-I were labeled with $^{125}$I by the method of Bilheimer et al. (1972) *Biochim. Biophys. Acta* 260: 212–221. Mice were placed on a modified Thomas-Hartroft atherogenic diet (#TD88051; Teklad, Madison, Wis.) for four weeks at which time daily intraperitoneal injections of peptide or protein dissolved in 200 μl phosphate-buffered saline (PBS) were begun. Animals injected with MoAI or human apo A-I received 50 μg per animal; those injected with 5F received 20 μg. Animals were not fasted for the kinetic studies and blood samples were taken under xylazine:ketamine anesthesia from the retro-orbital sinus at 15, 30, and 45 minutes, and 1, 1.5, 2, 3, 4, 6, 8, 12, and 24 hours following injection. Each animal provided three blood samples at different time points (all retro-orbital and alternating eyes), and at least three samples were collected (from different animals) at each time point. Samples were collected into heparinized capillary tubes, then placed in microcentrifuge tubes; the plasma was separated by centrifugation. Duplicate 10 μl aliquots of each sample were taken for radioactivity determination, using gamma counting (Cobra; Packard Instruments, Downers Grove, Ill.) for 10 minutes per sample. Total plasma volume was calculated as 4.2% body weight. Each sample was expressed as percent of injected CPM in total plasma. Free $^{125}$I was determined by trichloroacetic acid (TCA) precipitation (1 ml of 10% TCA per 10 μl plasma sample). Fitting to the kinetic model was done using all data points, rather than averages at each time point (PKAnalyst, MicroMath Scientific Software, Salt Lake City, Utah).

Injection Protocol and Sample Collection for Lesion Studies—

Mice were acquired at six weeks of age, and randomized into groups of 20, except that a negative control group of 10 received no treatments and was given standard rodent chow. At eight weeks of age, the treatment groups were placed on a modified Thomas-Hartroft atherogenic diet (#TD88051; Teklad, Madison, Wis.), and injections were begun. The diet was stored at 4° C. and was used for no longer than three months after the manufacture date in order to minimize lipid oxidation. Animals were injected intraperitoneally daily for 16 weeks, including weekends and holidays. Twenty Mice in each group received daily injections of 200 μl PBS (as positive controls), or 20 μg 5F in 200 μl PBS, or 50 μg MoAI in 200 μl PBS.

Lyophilized 5F peptide was prepared in vials, with each bottle containing sufficient peptide for one day's injection. The 5F peptide was lyophilized in PBS, and was dissolved in autoclaved Milli-Q water (Millipore Corp., Bedford, Mass.) on the day of injection. The injection volume for all groups was maintained at 200 μl/mouse per day.

Blood samples were taken under anesthesia by retro-orbital bleeding at study entry (pre-diet) and at the time of organ harvesting. At the end of the study (week 16), at the last bleeding, the heart and the liver were excised. The hearts were kept in 0.9% saline solution for about 1 hour to eliminate blood and to permit the heart muscle to relax. They were then fixed in phosphate-buffered 4% formaldehyde for at least one week until sectioned. The livers were removed and weighed.

Histological Evaluation—

Histological evaluations were performed according to the method of Paigen et al. (Paigen et al. (1990) *Arteriosclerosis* 10: 316–323) with some modifications. Briefly, hearts were fixed for at least one week in the phosphate-buffered formaldehyde solution. After removing the lower ⅔ of the hearts, the remaining tissue was frozen in OCT medium (Tissue-Tek, Miles Inc., Elkhart, Ind.) and sectioned in a cryostat at −20° C. Alternate 20 μm sections were saved on slides, and observed for the beginning of the aortic root. Sections were then collected for an additional 600 μm, or until the aortic cross-section was rounded and the valve cusps were no longer evident. Slides were stained with Oil Red O, and counterstained with hematoxylin. Stained lesion cross-sectional areas were measured in consecutive slides 80 μm apart by image analysis (SigmaScan Pro, SPSS Scientific, Chicago, Ill.), and the average lesion area was determined for each aortic sinus over the 400 μm length (five slides) providing the greatest mean lesion area.

Cocultures, Monocyte Isolation, Isolation of Lipoproteins, Determination of Lipid Hydroperoxides, and Monocyte Chemotactic Activity—

Cocultures of human artery wall cells, monocyte isolation, isolation of lipoproteins by ultracentrifugation from the plasma of normal human donors or from mouse plasma by FPLC, and determination of lipid hydroperoxides and monocyte chemotactic activity were performed according to standard methods. All human subject participation was with informed consent approved by the UCLA Human Subjects Protection Committee. The protocol for testing mouse lipoproteins in the coculture was also performed as follows: Briefly, LDL and HDL were isolated by FPLC from mouse plasma from mice fed the atherogenic diet and injected with vehicle (PBS), or with peptide 5F at 20 μg/mouse/day. The cocultures were treated with human LDL at 200 μg/ml LDL protein, or mouse LDL at 200 μg/ml or with 200 μg/ml human LDL+human HDL at 350 μg/ml of HDL protein or mouse HDL at 300 μg/ml or with mouse HDL alone at 300 μg/ml. The cocultures were incubated with or without the above additions for 8 hrs at 37° C. in the presence of 10% lipoprotein deficient serum (LPDS). The supernatants were collected and analyzed for Auerbach lipid hydroperoxide equivalents. The cocultures were then washed and incubated with fresh culture medium without serum or LPDS for an additional 8 hrs. The conditioned medium was collected and analyzed for monocyte chemotactic activity.

Chemical and Analytical Methods—Column Cholesterol Lipoprotein Profiles (CLiP)—

Plasma cholesterol lipoprotein profiles were measured using our recently-developed CLiP method (Garber et al. (2000) *J. Lipid Res.* 41:1020–1026). Briefly, 5 to 10 μl of plasma were analyzed using a single Superose 6 (Pharmacia, Piscataway N.J.) column. Immediately following the column, cholesterol reagent was introduced through a mixing tee, and the eluent:reagent mixture entered a post-column reaction coil. Cholesterol content of the eluent mixture was spectrophotometrically detected at 500 nm, and data points were collected into a computer. The resulting profiles were decomposed into component peaks and analyzed for relative area using PeakFit (SPSS Science, Chicago, Ill.); absolute cholesterol values for total cholesterol and each component peak were determined by comparison with a control sample of known values. In some cases fractions were collected to determine distribution of radioactivity. The CLiP method allowed analysis of individual mouse samples, avoiding the use of pooled samples.

Antibody Detection—

To determine whether daily injections of peptides elicited any immune response in mice, indirect ELISA titration (Engvall (1980) *Meth. Enzymol.* 70:419–439) was carried out with plasma taken from mice at the time of organ collection (following sixteen weeks of daily injection). Plates were coated with the injected peptides or MoAI (10 µg/ml). Plates were incubated overnight. After thorough washing with borate buffered saline (pH 8.2) containing 0.05% Tween 20, and blocking with buffer (0.1% gelatin and 0.1% BSA in borate buffer) for 1 h, 200 µl of the diluted mouse plasma (1:100 dilution) samples were serially diluted 1:1 with borate-buffered saline. Biotinylated goat antibody to mouse IgG (0.1 µg/ml) was then added to the wells and the plates were treated with SA-HRP (Streptavidin-horse radish peroxidase) for an hour and developed with ABTS and peroxide as substrate. The plates were incubated overnight at room temperature after every addition of antigen/antibody and washed thoroughly with borate buffered saline (pH 8.2) containing 0.05% Tween 20, and blocked with buffer (0.1% gelatin and 0.1% BSA in borate buffer) for 1 h before the next addition.

Statistical Methods—

Treatment groups were compared by two-tailed t-tests or one way analysis of variance (where the data were normally distributed), or by one way analysis of variance on ranks (SigmaStat; SPSS Science, Chicago, Ill.). Kinetics of peptide or protein turnover were analyzed by fitting to a first order one-compartment kinetic model assuming non-equal input and output rates (PKAnalyst; MicroMath Scientific Software, Salt Lake City, Utah).

Results

Kinetic Studies—

The kinetics of the clearance of peptide 5F and human and mouse apo A-I from mouse plasma following intraperitoneal injection are summarized in Table 2.

TABLE 2

Summary of fitted data from kinetic experiments

| Injected Material | T½ (h) | Time (h) to max. CPM | Max. % in plasma | r² |
|---|---|---|---|---|
| Human apo A-I (50 µg/mouse) | 15.6 | 3.61 | 23.7 | 0.947 |
| Mouse apo A-I (50 µg) | 15.7 | 1.74 | 13.5 | 0.928 |
| 5F (20 µg) | 6.22 | 2.36 | 14.29 | 0.895 |

Data shown represent results of fitting data to a first order one-compartment kinetic model assuming unequal input and output rates (PKAnalyst; MicroMath Scientific Software, Salt Lake City, UT). Abbreviations: T½: half time of clearance from plasma; Max. % in plasma: percent of injected dose found in total plasma at peak levels; r²: goodness of fit statistic of the kinetic model.

Figure 1B:
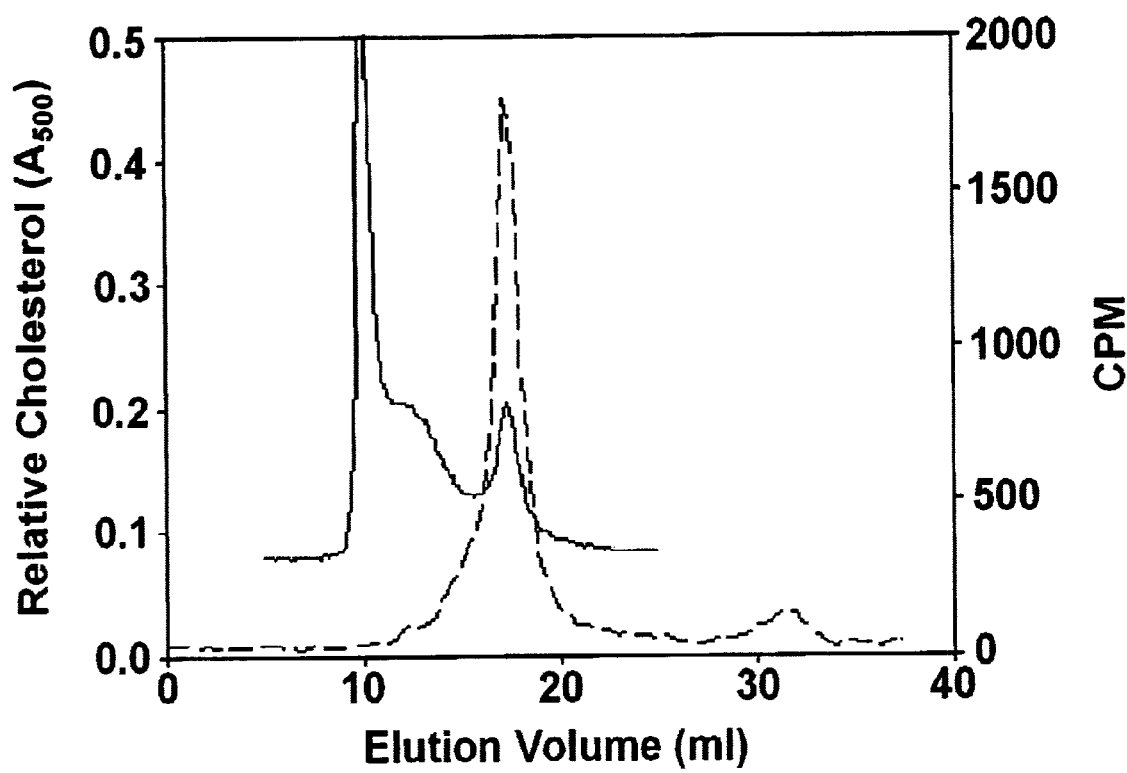
Figure 1C:
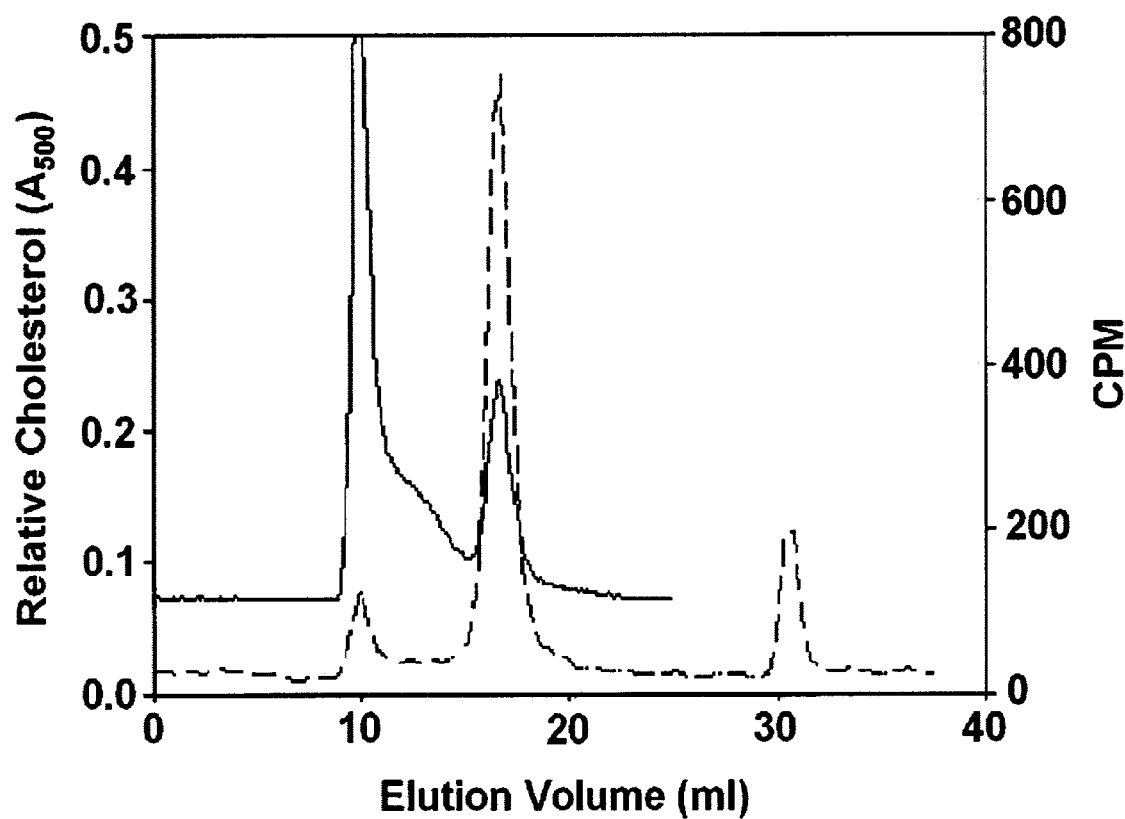

Human and mouse apo A-I had greatly prolonged clearance compared with the 5F peptide. Human apo A-I and 5F had longer times to peak plasma levels than did mouse apo A-I, although peak levels achieved were generally similar (human apo A-I reached higher peak levels than did the other materials). Analysis of plasma samples by column chromatography demonstrated that peptide 5F and apo A-I (both human and mouse) associated with plasma lipoproteins, especially with particles in the HDL-sized region (FIG. 1). The HDL:VLDL ratio of peptide radioactivity 1.5 h following injection of 5F was 4.19±0.58 (n=3, p<0.05). Similar results were found 5 h following injection of 5F (6.44±1.10, p<0.02). The injected peptide initially had less than 3% free $^{125}I$ by TCA precipitation. However, 1.5 hours after injection, free $^{125}I$ radioactivity in the plasma as a percent of total eluted radioactivity was substantially greater for 5F being 26.9±9.4% and at 5 hours 34.4±4.8%, reflecting the expected clearance of lipoproteins and lipoprotein-associated peptides. The rate of increase in the radioactivity due to free iodine from 1.5 to 5 hours was less than that from injection to 1.5 hours, possibly suggesting considerable initial degradation of the peptide in the peritoneal cavity.

Survival and Gross Morphology on the Chow or Atherogenic Diets—

Only three mice died from unexplained causes during the course of the prolonged diet studies. Two of the animals had been receiving MoAI, and one was receiving 5F peptide. At the time of organ collection, no gross morphological differences were observed between the groups. Livers were enlarged in all animals fed the atherogenic diet, but neither liver weights nor liver weight as a percent of body weight were different between groups (Table 3). All animals on the atherogenic diet (including PBS-injected animals) had lower body weights than the chow-fed controls (Table 3).

TABLE 3

Body and liver weights following treatment.

| Diet & Subgroup | Body Weight (g) | Liver Weight (g) | Liver:Body (percentage) |
|---|---|---|---|
| Chow | 23.38 ± 0.52 | 0.99 ± 0.02 | 4.24 ± 0.04% |
| Atherogenic | | | |
| PBS (n = 14) | 20.55 ± 0.32* | 1.60 ± 0.04 | 7.84 ± 0.26% |
| 5F (n = 15) | 21.60 ± 0.28 | 1.61 ± 0.04 | 7.46 ± 0.23% |
| MoAI (n = 14) | 21.16 ± 0.34 | 1.72 ± 0.04 | 8.15 ± 0.23%* |

Data shown are mean ± SEM of weights taken at the time of organ harvesting (after 16 weeks of treatment). The chow-fed animals received no injections. The other mice were maintained on the atherogenic diet as described in Methods. The PBS group received intraperitoneal injections of 200 µl phosphate-buffered saline daily. The 5F group received intraperitoneal injections of 20 µg 5F in 200 □1 PBS daily and the MoAI group received 50 µg MoAI in 200 µl PBS daily.
*p < 0.05 vs 5F; two-tailed t-test Antigenicity—

Blood samples taken at the conclusion of the 16-week injection period were tested for the presence of antibodies against the peptides. No antibodies were detected against peptide 5F or against MoAI (data not shown). Cross experiments, where the ELISA plates were coated with peptides or protein which was not injected into the series of animals, produced results essentially identical to those in the direct determination of the presence of antibodies (data not shown).

Lipoprotein and Apolipoprotein Characterization—

Total and lipoprotein cholesterol values as determined by the CLiP method are presented in Table 3. Accuracy of total cholesterol values was confirmed by a manual cholesterol assay (Cholesterol 1000; Sigma, St. Louis, Mo.) (data not shown). No significant differences in total or lipoprotein-fraction cholesterol levels were seen between the treatment groups. However, when lipoprotein fractions were expressed as a percent of total cholesterol (Table 4), HDL-cholesterol comprised a significantly lower percentage in the 5F and MoAI groups compared with the PBS group.

TABLE 4

Total and lipoprotein cholesterol levels (mg/dl and percent of total cholesterol) after 16 weeks of chow or atherogenic diet.

|  | VLDL | IDL + LDL | HDL | TC |
|---|---|---|---|---|
| Chow Diet | 11.66 ± 2.34 | 23.68 ± 3.51 | 37.30 ± 2.52 | 72.64 ± 5.58 |
|  | (16.61 ± 3.55%) | (31.66 ± 3.61%) | (51.73 ± 1.75%) |  |
| Atherogenic Diet |  |  |  |  |
| PBS | 88.36 ± 5.48 | 75.82 ± 7.64 | 24.36 ± 2.19 | 188.54 ± 14.22 |
|  | (47.26 ± 1.37%) | (39.83 ± 1.34%) | (12.91 ± 0.68%) |  |
| 5F | 100.34 ± 15.72 | 83.37 ± 8.15 | 17.92 ± 2.91 | 201.63 ± 25.21 |
|  | (47.96 ± 3.26%) | (42.80 ± 2.51%) | (9.24 ± 1.18%*) |  |
| MoAI | 100.08 ± 9.73 | 87.86 ± 8.34 | 19.50 ± 3.07 | 207.45 ± 16.94 |
|  | (48.23 ± 2.75%) | (42.44 ± 2.46%) | (9.34 ± 1.19%*) |  |

Data are expressed as mean mg/dl ± SEM and, in parentheses, as percent of total cholesterol. Abbreviations: VLDL, very low density lipoprotein; IDL, intermediate density lipoprotein; LDL, low density lipoprotein; HDL, high density lipoprotein; TC, total cholesterol; MoAI, mouse apo A-I; PBS, Phosphate buffered saline. The chow-fed animals received no injections. The other mice were maintained on the atherogenic diet as described in Methods. The PBS group received intraperitoneal injections of 200 µl PBS daily. The 5F group received intraperitoneal injections of 20 µg 5F in 200 µl PBS daily and the MoAI group received 50 µg MoA-I in 200 µl PBS daily. Numbers of animals are as shown in Table 3.
*p < 0.05 or less compared with PBS by two-tailed t-test.

Interaction of Mouse Lipoproteins With Human Artery Wall Cells—

Figure 2A:
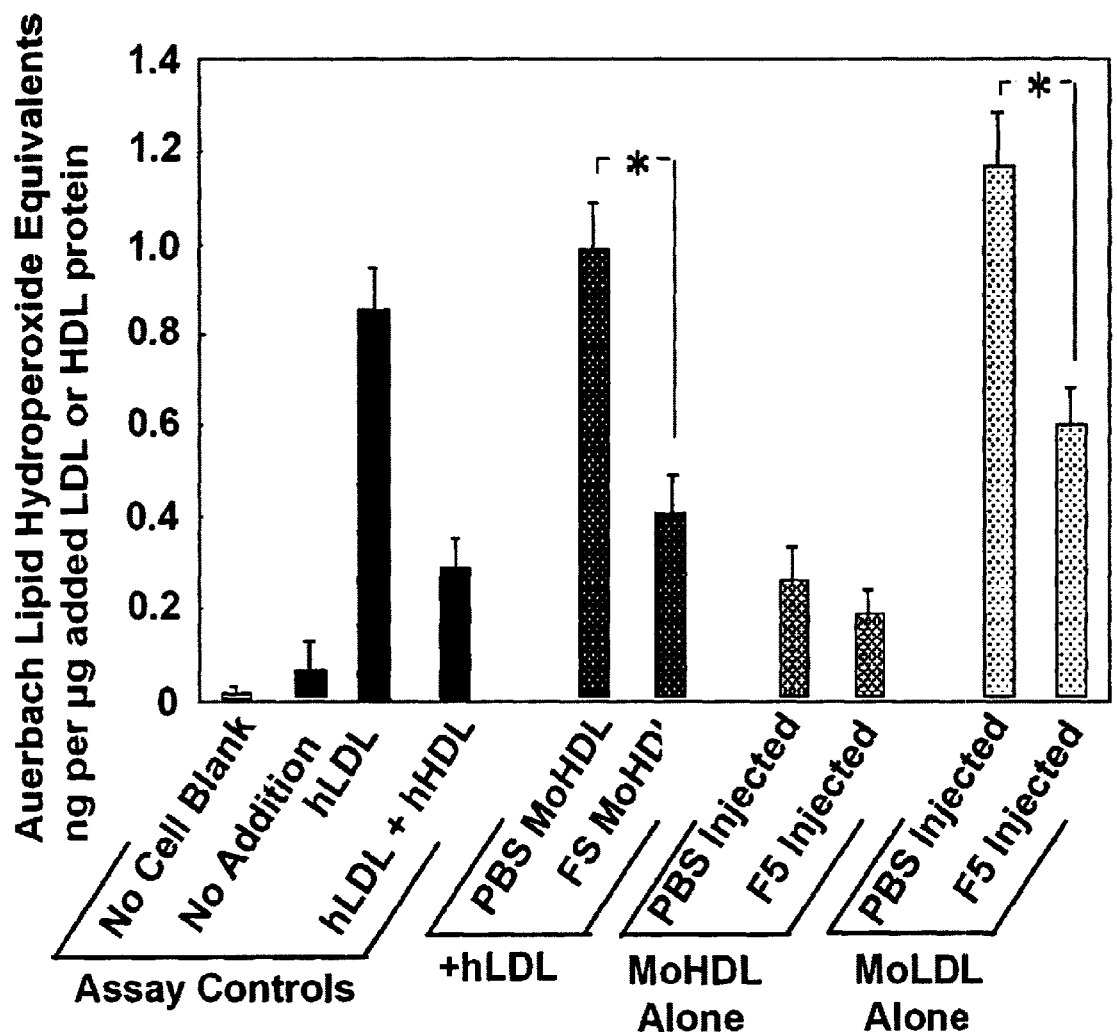
FIG. 2A and FIG. 2B illustrate the interaction of mouse lipoproteins with human artery wall cells. LDL and HDL were isolated by FPLC from the plasma of mice fed the atherogenic diet and injected with vehicle (PBS), or with peptide 5F at 20 μg/mouse/day. The cocultures were treated without (No Addition) or with human LDL (hLDL) at 200 μg/ml LDL protein, or mouse LDL (MoLDL) at 200 μg/ml or with 200 μg/ml human LDL+human HDL (hHDL) at 350 μg/ml of HDL protein or mouse HDL (MoHDL) at 300 μg/ml. The cocultures were incubated with the above additions for 8 hrs at 37° C. in the presence of 10% lipoprotein deficient serum (LPDS). The supernatants were collected and analyzed for Auerbach lipid hydroperoxide equivalents (FIG. 2A). The cocultures were then washed and incubated with fresh culture medium without serum or LPDS for an additional 8 hrs. The conditioned medium was collected and analyzed for monocyte chemotactic activity (FIG. 2B). A no cell blank (No Cell Blank) is included in both panels for comparison.
Figure 2B:
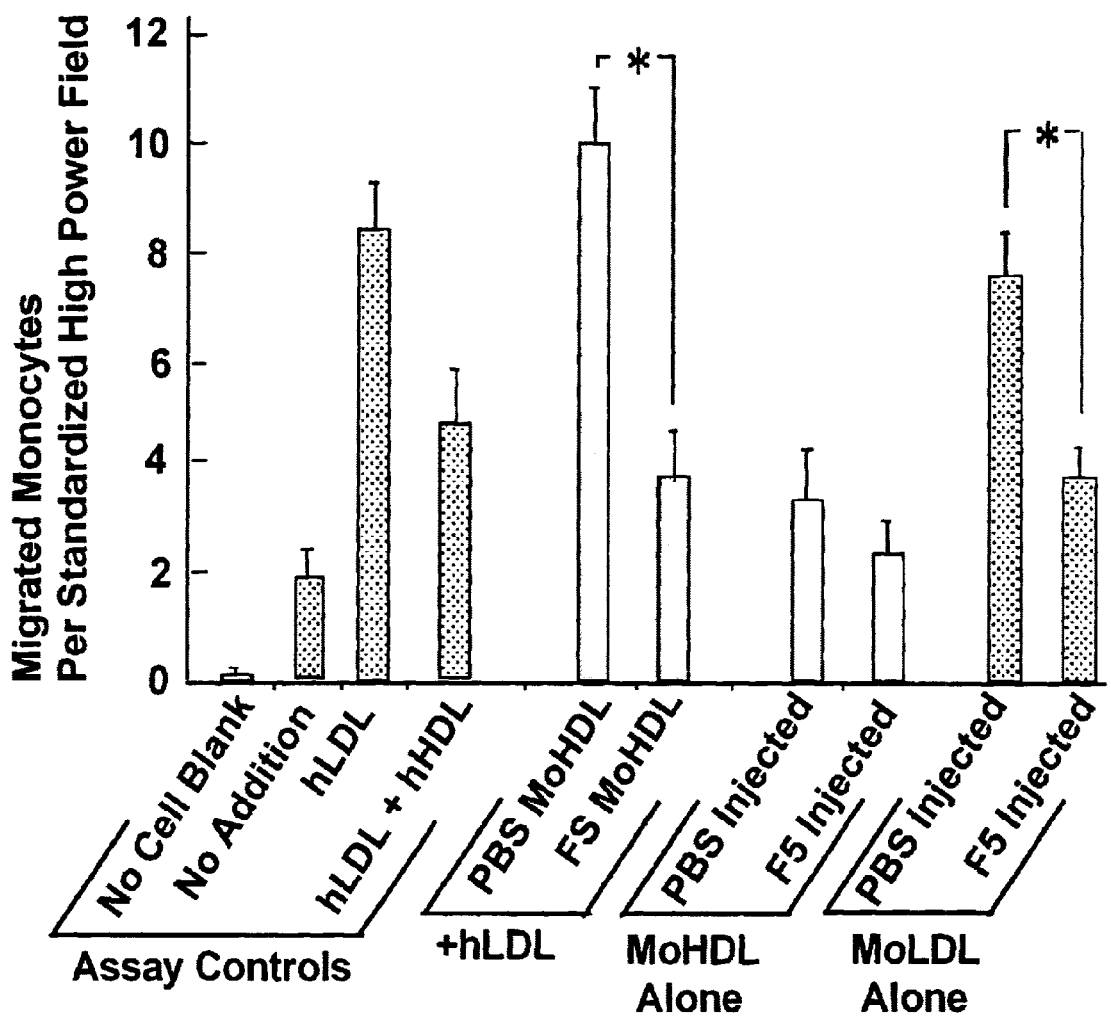

We recently discovered that normal HDL inhibits three steps in the formation of mildly oxidized LDL. In those studies (see, copending application U.S. Ser. No. 09/541,468, filed on Mar. 31, 2000) we demonstrated that treating human LDL in vitro with apo A-I or an apo A-I mimetic peptide (37pA) removed seeding molecules from the LDL that included HPODE and MPETE. These seeding molecules were required for cocultures of human artery wall cells to be able to oxidize LDL and for the LDL to induce the artery wall cells to produce monocyte chemotactic activity. We also demonstrated that after injection of apo A-I into mice or infusion into humans, the LDL isolated from the mice or human volunteers after injection/infusion of apo A-I was resistant to oxidation by human artery wall cells and did not induce monocyte chemotactic activity in the artery wall cell cocultures. FIG. 2 demonstrates that HDL from the mice in the present study that were fed the atherogenic diet and injected with PBS failed to inhibit the oxidation of human LDL (FIG. 2A) and failed to inhibit LDL-induced monocyte chemotactic activity (FIG. 2B) in human artery wall cocultures. In contrast, HDL from mice fed the atherogenic diet and injected daily with peptide 5F was as effective in inhibiting human LDL oxidation and preventing LDL-induced monocyte chemotactic activity in the cocultures as was normal human HDL. FIG. 2 also shows that LDL taken from mice fed the atherogenic diet and injected daily with PBS was more readily oxidized and more readily induced monocyte chemotactic activity than LDL taken from mice fed the same diet but injected with 20 µg daily of peptide 5F. No cytotoxicity was noted in the artery wall cells treated with any of the lipoproteins (data not shown). Similar results were obtained in three of three separate experiments (data not shown).

Lesion Formation—

Figure 3:
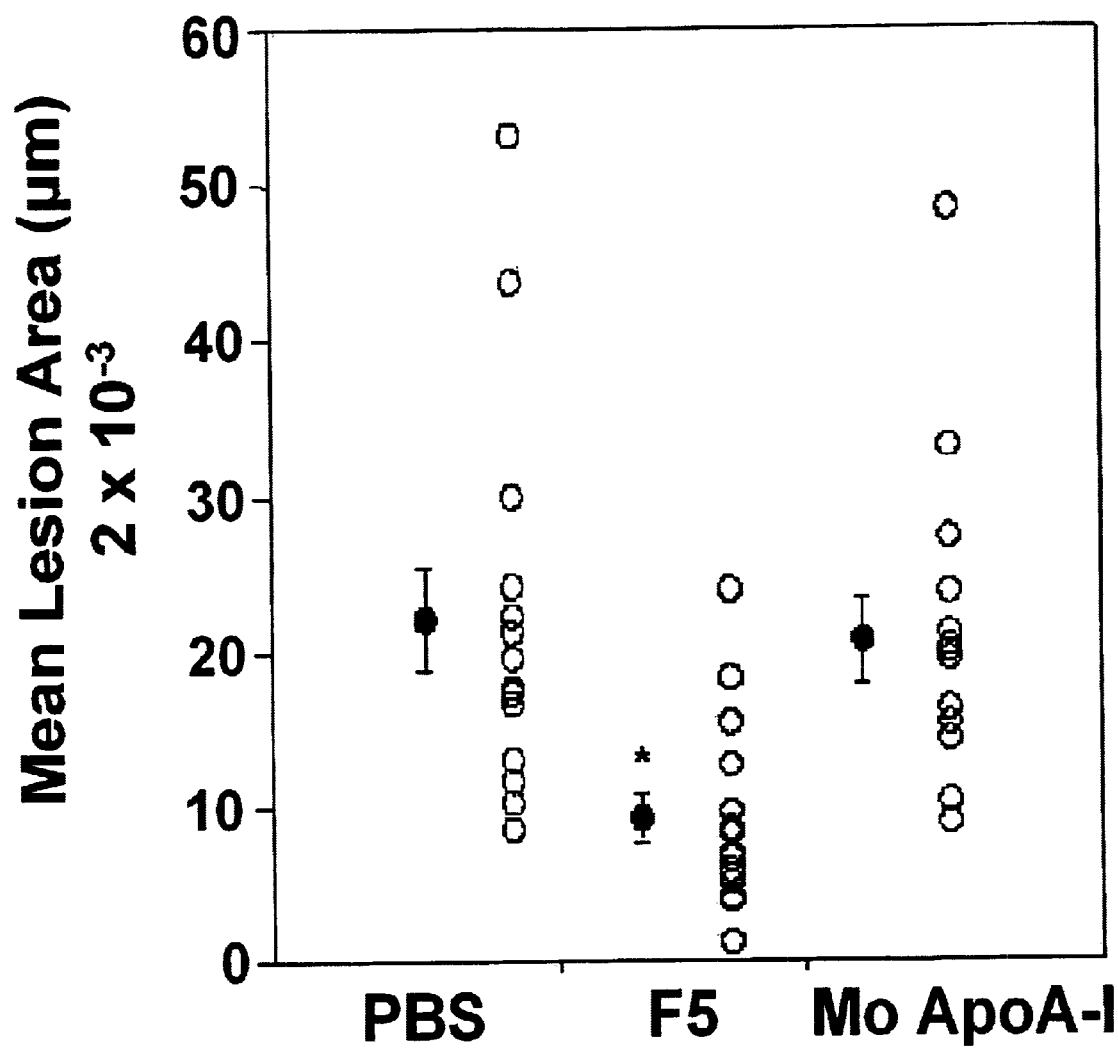
FIG. 3 shows mean lesion cross-sectional areas. Data shown represent the mean lesion cross-sectional area for each animal (○ and the mean±SEM of all animals in each group (●) with error bars. Abbreviations: PBS, mice fed the atherogenic diet and injected daily with 200 μl phosphate-buffered saline; 5F, mice fed the atherogenic diet and injected daily with 20 μg of 5F in 200 μl PBS; MoAI, mice fed the atherogenic diet and injected daily with 50 μg of mouse apo A-I in 200 μl PBS. *=p<0.002 as determined by two-tailed t-test. A significant difference was also shown using one way analysis of variance on ranks (p<0.001).

Mean lesion cross-sectional areas are presented in FIG. 3. As expected, no lesions were observed in the group given normal mouse chow (data not shown). As previously reported (Paigen et al. (1990) *Arteriosclerosis* 10: 316–323), considerable variations in lesion area were observed in all groups receiving the atherogenic diet. However, the 5F-injected animals had significantly lower mean lesion area than PBS-injected animals, whether analyzed by two-tailed t-test (p<0.002) or by one-way analysis of variance on ranks (p<0.001; determined due to the non-normal distribution of mean lesion areas). MoAI injection produced no difference in lesion area compared with PBS injection, and lesion area was significantly greater than in 5F-injected animals, both by t-test (p<0.002) and by one way analysis of variance on ranks (p<0.001).

Discussion

The studies presented here demonstrated that this peptide 5F entered the plasma after interperitoneal injection and achieved plasma levels that were roughly comparable to MoAI, but less than human apo A-I (Table 2 and FIG. 1). The plasma clearance half-time of 5F was shorter than either mouse or human apo A-I after peritoneal injection. After injection the majority of 5F was found in the region of HDL (FIG. 1), despite the fact that the preponderance of circulating cholesterol was in the VLDL-, IDL-, and LDL-sized regions on the atherogenic diet.

Plasma cholesterol levels and distributions were not significantly different among the injected groups on the atherogenic diet (Table 4). However, when the lipoprotein fractions were expressed as a percent of total cholesterol (Table 4), HDL-cholesterol comprised a significantly lower percentage in the 5F and MoAI groups compared with the PBS group.

Normal HDL inhibits three steps in the formation of mildly oxidized LDL. We demonstrated that treating human LDL in vitro with apo A-I or an apo A-I mimetic peptide removed seeding molecules from the LDL that included HPODE and BPETE. These seeding molecules were required for cocultures of human artery wall cells to be able to oxidize LDL and for the LDL to induce the artery wall cells to produce monocyte chemotactic activity (see copending copending application U.S. Ser. No. 09/541,468, filed on Mar. 31, 2000). We also demonstrated that after injection of apo A-I into mice or infusion into humans, the LDL isolated from the mice or human volunteers after injection/infusion of apo A-I was resistant to oxidation by human artery wall cells and did not induce monocyte chemotactic activity in the artery wall cell cocultures. In the present studies, HDL from mice that were fed the atherogenic diet and injected with PBS failed to inhibit the oxidation of human LDL (FIG. 2A) and failed to inhibit LDL-induced monocyte chemotactic activity (FIG. 2B) in the human artery wall cocultures. In stark contrast, HDL from mice fed the same atherogenic diet but injected with peptide 5F was found to be as effective in inhibiting human LDL oxidation and preventing LDL-induced monocyte chemotactic activity in the cocultures as was normal human HDL (FIG. 2). LDL taken from mice fed the atherogenic diet and injected with 5F was less readily oxidized and induced less monocyte chemotactic activity than LDL taken from mice fed the same diet but injected with PBS (FIG. 2). It is possible that 5F interacted with LDL in the circulation (either before or after associating with HDL) and removed seeding molecules necessary for LDL oxidation and LDL-induced monocyte chemotactic activity in a manner similar to that described in vitro for a related peptide, 37pA (copending copending application U.S. Ser. No. 09/541,468, filed on Mar. 31, 2000).

The in vitro responses of human artery wall cells to HDL and LDL from mice fed the atherogenic diet and injected with peptide 5F are consistent with the protective action of 5F in vivo. Despite, similar levels of total cholesterol, LDL-cholesterol, IDL+VLDL-cholesterol, and lower HDL-cholesterol as a percent of total cholesterol, the animals fed the atherogenic diet and injected with 5F had significantly lower lesion scores (FIG. 3). These results are somewhat analogous to those of Shah et al. (Shah et al. (1998) *Circulation* 97:780–785) who found that, despite persistence of hypercholesterolemia, apo A-I$_{Milano}$ prevented progression of atherosclerotic lesions in apo E-deficient mice.

The reason that human apo A-I has been used successfully to prevent/reduce atherosclerosis in animals (Wilson et al. (1988) *Arteriosclerosis* 8: 737–741; Rubin et al. (1991) *Nature* 353:265–267; Paszty et al. (1994) *J. Clin. Invest.* 94:899–903; Plump et al. (1994) *Proc. Natl. Acad. Sci. USA* 91:9607–9611; Shah et al. (1998) *Circulation* 97:780–785) but injection of MoAI at a dose of 50 μg daily in these studies did not is not clear. It has been shown that MoAI does not form protein:lipid complexes as stable as does human apo A-I (Gong et al. (1994) *Biochim. Biophys. Acta* 1213:335–342). Mouse HDL has also been shown to be more easily denatured by guanidine hydrochloride than human HDL (Gong et al. (1994) *Biochim. Biophys. Acta* 1213:335–342) suggesting that amphipathic helical peptides might displace MoAI more easily from mouse HDL than human apo A-I from human HDL. These differences may or may not explain why MoAI did not significantly reduce lesions in this study. It may also be that a higher dose of MoAI is required under the conditions that we employed. In any event, the 5F peptide was highly effective under these conditions and MoAI was not.

The ELISA analysis of plasma at the conclusion of the injection protocol indicated that antibodies were not formed against the 5F peptide. This was not surprising in that lipid-associating peptides have been shown not to produce antibodies, presumably because these peptides bind lipids in such a way as to prevent the exposure of epitopes necessary to elicit an immune response (Muranishi (1997) *J. Pharm. Soc. Japan* 117:394–404; Fricker and Drewer (1996) *J Peptide Sci.* 2:195–211).

A preliminary study by us suggested that transgenic mice expressing a class A amphipathic helical peptide (37pA) with theoretically less lipid affinity than the peptide used in this study may have been resistant to atherosclerosis (Garber et al. (1997) *Circulation* 96:I-490). The current study suggests that peptide 5F likely has great potential for elucidating the mechanisms involved in atherogenesis and also has therapeutic potential.

Example 2

This example demonstrates the efficacy of D peptides of this invention. Human aortic wall cocultures were incubated with medium alone (LDL, NO CELLS or CELLS, NO LDL), control LDL from normal subjects at 250 μg/ml (LDL) and LDL plus control HDL from normal subjects at 350 μg/ml (+HDL). Other cocultures were incubated with the control LDL together with varying amounts (micrograms shown on the abscissa) of either D-2F, or L-2F (third panel from the left, 2F) or D-37-pA or L-37pA (last panel on the right, 37pA). The data represent mean±SD of values obtained from quadruplicate cocultures. Values for HDL or added peptides were all significantly different from LDL alone (first panel on the left) at the level of p<0.01.

Figure 4:
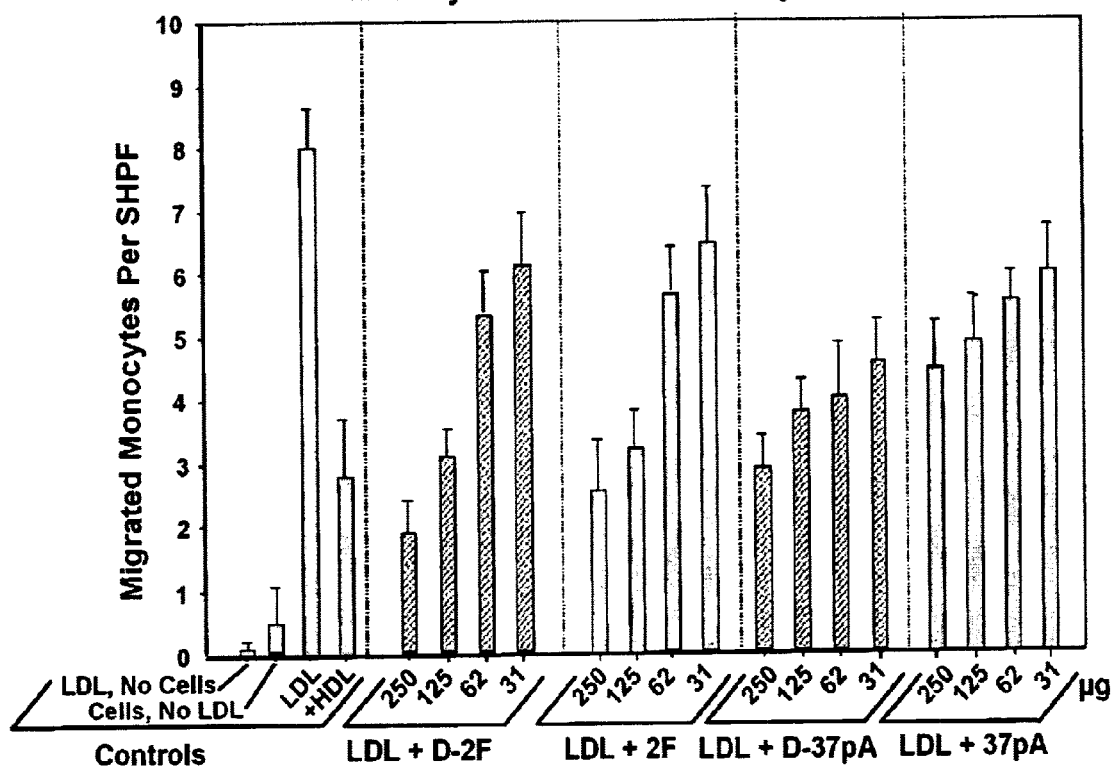
FIG. 4 shows that both the D and L isomers of apo A-I peptide mimetics prevent monocyte chemotactic activity induced by mildly oxidized LDL in vitro. Medium alone (LDL, NO CELLS or CELLS, NO LDL), control LDL from normal subjects at 250 μg/ml (LDL), and LDL plus control HDL from normal subjects at 350 μg/ml (+HDL). Other cocultures were incubated with the control LDL together with varying amounts (micrograms shown on the abscissa) of either D-2F, or L-2F (third panel from the left, 2F) or D-37-pA or L-37pA (last panel on the right, 37pA). The data represent mean±SD of values obtained from quadruplicate cocultures. Values for HDL or added peptides were all significantly different from LDL alone (first panel on the left) at the level of p<0.01.

The cocultures were incubated for 4 hrs at 37° C. in the presence of 10% LPDS to produce mildly oxidized LDL. The supernatants were then discarded, the cocultures were washed and incubated with culture medium without serum or LPDS for an additional 4 hrs. This conditioned medium was collected and analyzed for monocyte chemotactic activity. As shown in FIG. 4, treating LDL with the D peptides in vitro prevents their oxidation by artery wall cells.

Figure 5A:
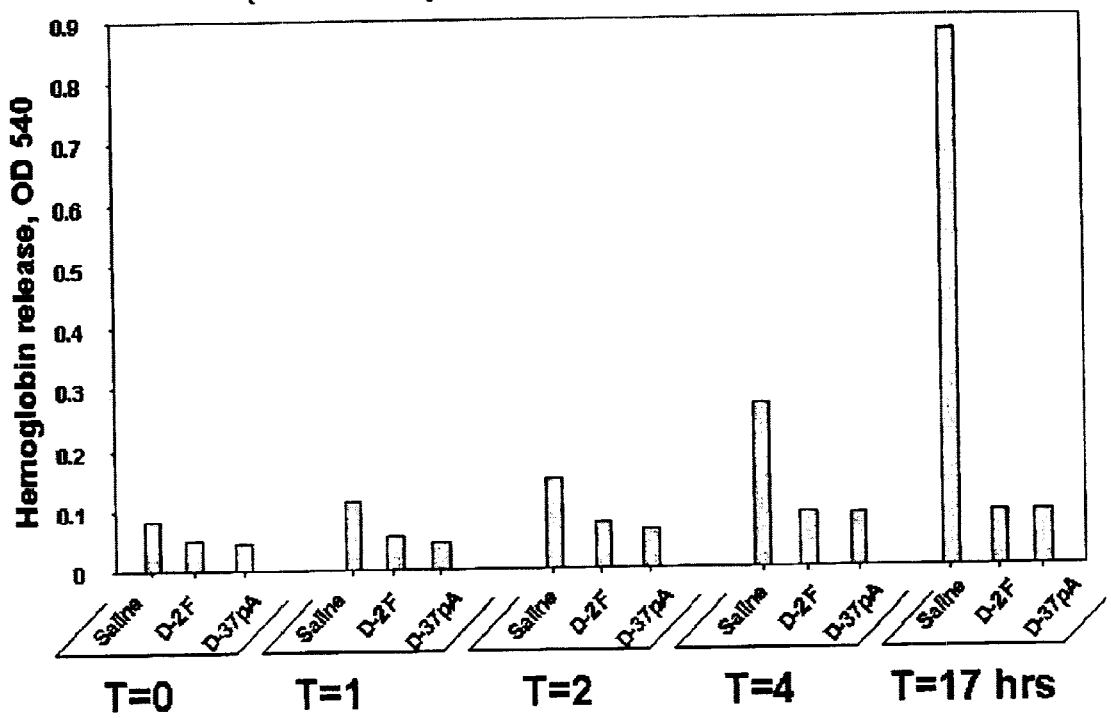
FIG. 5A and FIG. 5B illustrates results of in vitro red cell lysis assay at 18 hours (FIG. 5A) and at 48 hours (FIG. 5B). The asterisks reflect the presence of a significant difference (p<0001) between the red cell lysis for animals that received the vehicle vs those that received the peptides.
Figure 5B:
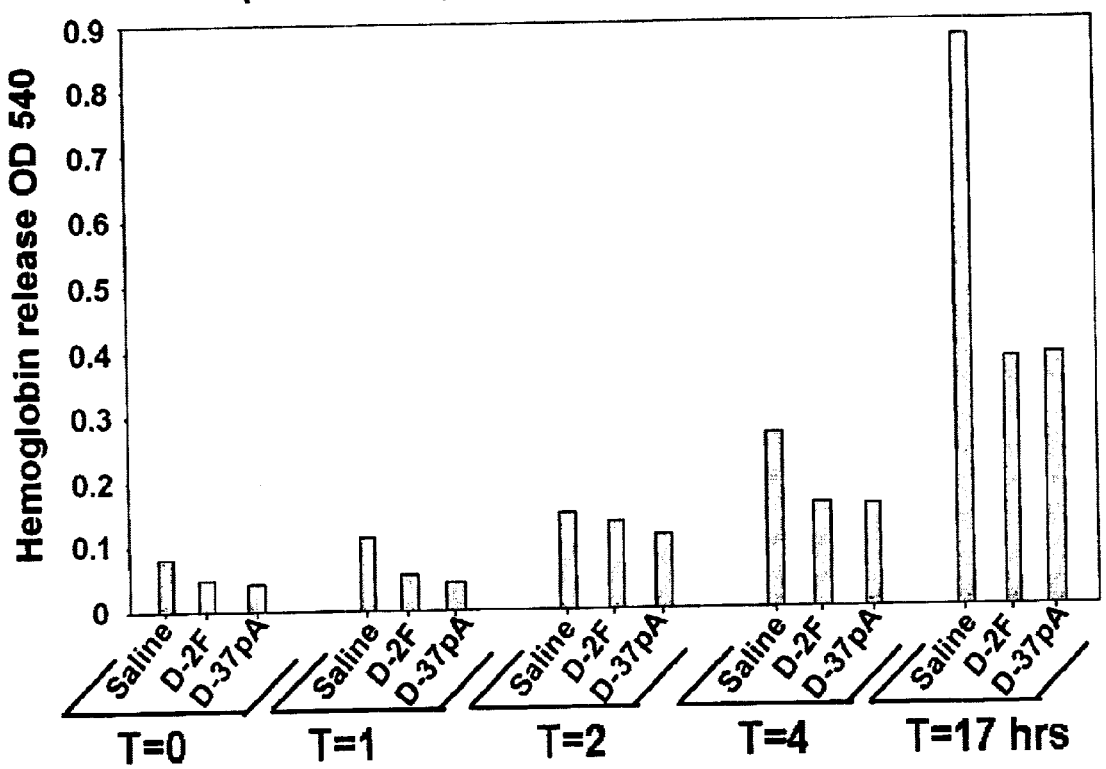

FIG. 5 demonstrates that giving the D peptides to mice renders their red blood cells resistant to hemolysis (a phenomenon due to oxidation as it can be prevented with Vitamin E, data not shown). Groups of LDL receptor deficient mice (n=3) commonly used as an animal model of atherosclerotic lesion formation were administered the D-peptides or the saline vehicle by gavage. Each animal was administered 100 μl of saline, 100 μg/100 μl of peptide D-2F or peptide D-37pA. Blood was collected from retroorbital sinus under mild anesthesia 17 n and 48 hrs later. Red cells were separated by centrifugation, were diluted to 10% hematocrit with PBS and incubated at 37° C. with gentle mixing. Aliquots were removed at time points t=0, 2, 6 and 18 hrs, cell pellets spun down and the optical density due to the released hemoglobin determined.

Figure 6:
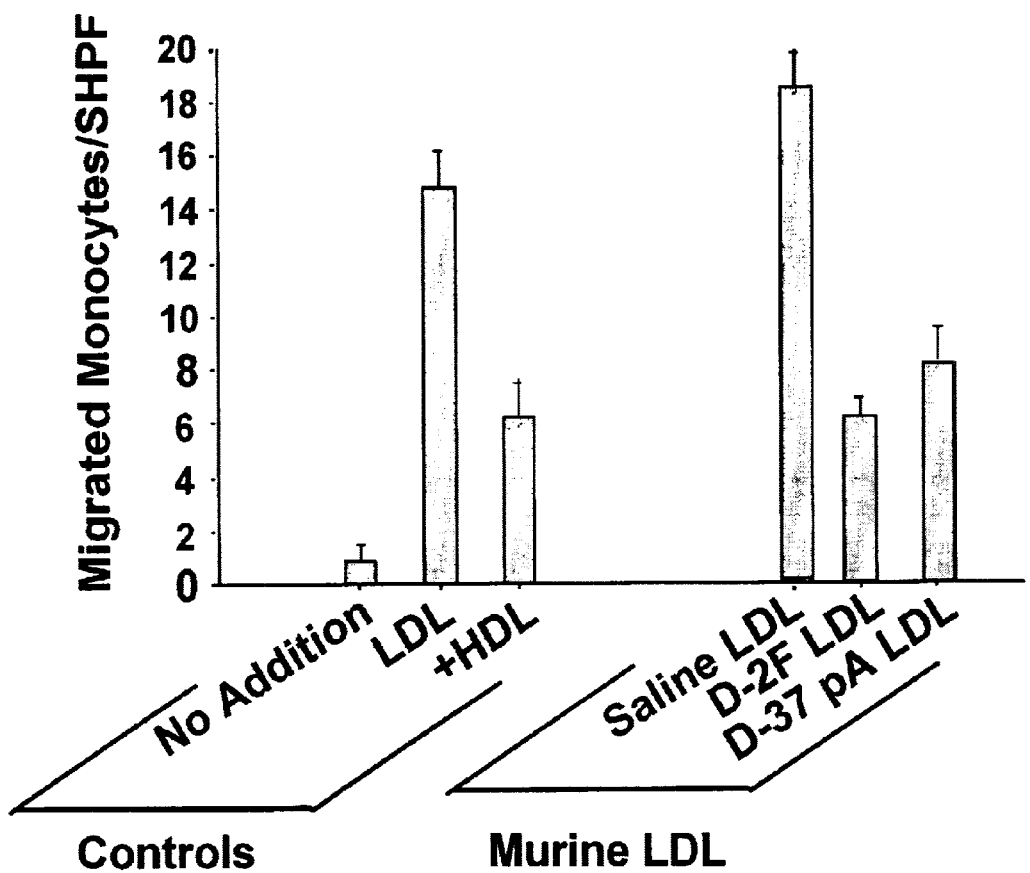
FIG. 6 illustrates the resistance of circulating LDL to oxidation following feeding of D-peptides. Groups of L receptor deficient mice (n=3) were administered the D-peptides or the saline vehicle by gavage. Each animal was given 100 μl of saline, 100 μg/100 μl of peptide D-2F or peptide D-37pA. Blood was collected from retroorbital sinus under mild anesthesia 17 hrs later. LDL was isolated from plasma by FPLC. Cocultures of artery wall cells were incubated with medium alone (NO ADDITION), control LDL from normal subjects (LDL), LDL plus control HDL from normal subjects (+HDL). Other cocultures were incubated with murine LDL following gavage with saline (SALINE LDL), with D-2F (D-2F LDL) or with D-37pA peptide (D-37pA LDL). The cocultures were incubated for 4 hrs at 37° C. in the presence of 10% LPDS. The supernatants were then discarded, the cocultures were washed and incubated with culture medium without serum or LPDS for an additional 4 hrs. This conditioned medium was collected and analyzed for monocyte chemotactic activity. The values are mean±SD of quadruplicate cocultures. The asterisks indicate p<0.001.

FIG. 6 demonstrates that administering the D peptides to mice by gavage and then isolating their LDL renders the LDL resistant to artery wall cell oxidation as measured by the monocyte chemotaxis bioassay.

Figure 7:
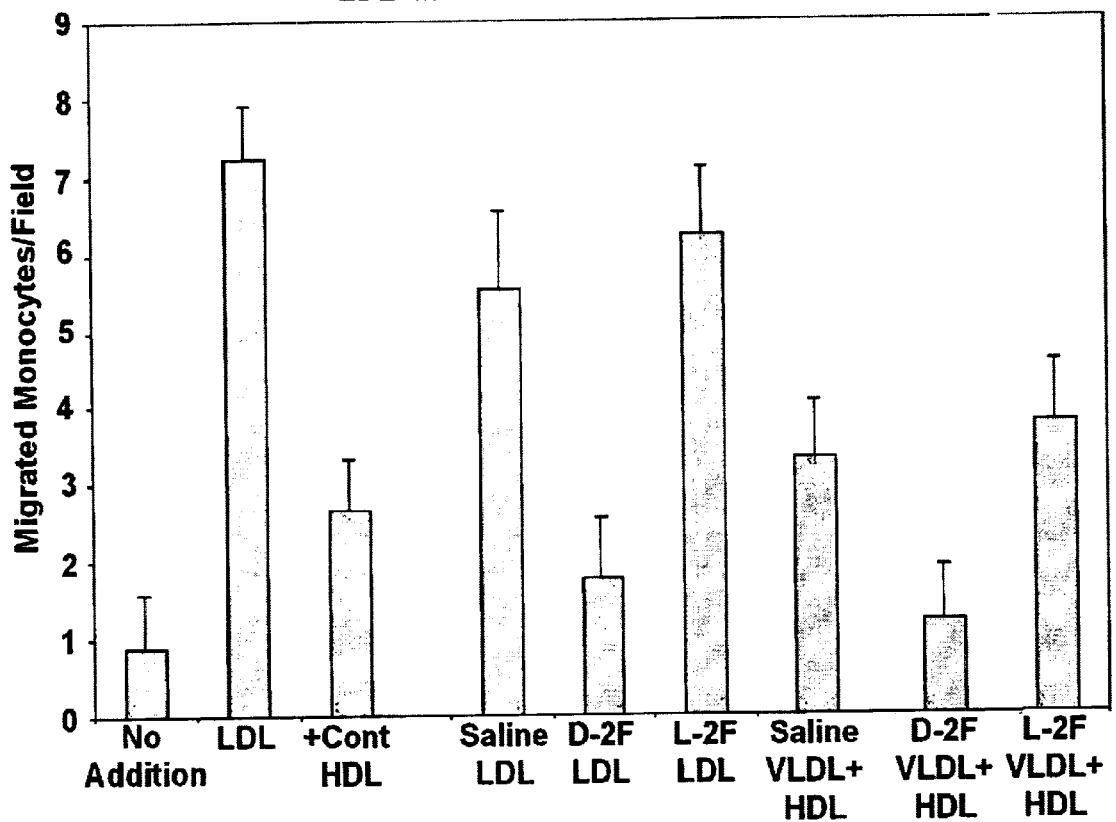
FIG. 7 illustrates the results of a chemotaxis assay comparing lipoproteins from mice given the D-form and or L-form peptides by gavage.

Another experiment demonstrated that the D-peptide was absorbed from the stomach and rendered LDL unable to induce monocyte chemotactic activity in our human artery wall cell coculture model while the L-peptide of 2F did not have this property. Either saline or 2F synthesized from D amino acids or from L amino acids was instilled in the stomachs of mice by gavage (instillation in the stomach by tube). After gavage the mice were bled and their LDL isolated and added to the human artery wall cell cocultures. The D-peptide when given by gavage protected the LDL as evidenced by the reduced monocyte chemotaxis induced by the LDL taken from the mice that received the D-2F peptide (D2FLDL) (synthesized from D amino acids), while the LDL taken from mice that received the L-2F (synthesized from the natural L amino acids) (L2FLDL) readily induced monocyte chemotaxis (see FIG. 7).

2F synthesized from L amino acids when presented to LDL in vitro was as effective as the 2F synthesized from the D amino acids (see FIG. 4). Thus, the difference in the results with this experiment where the peptides were given in vivo by gavage indicate that the 2F synthesized from D amino acids must have been absorbed intact from the stomach while the 2F peptide synthesized from the natural L amino acids must have been degraded in the stomach in the process of digestion and/or in the plasma as we hypothesized would be the case. In other studies we have not seen evidence of antibody formation against the D-2F peptide.

Figure 8A:
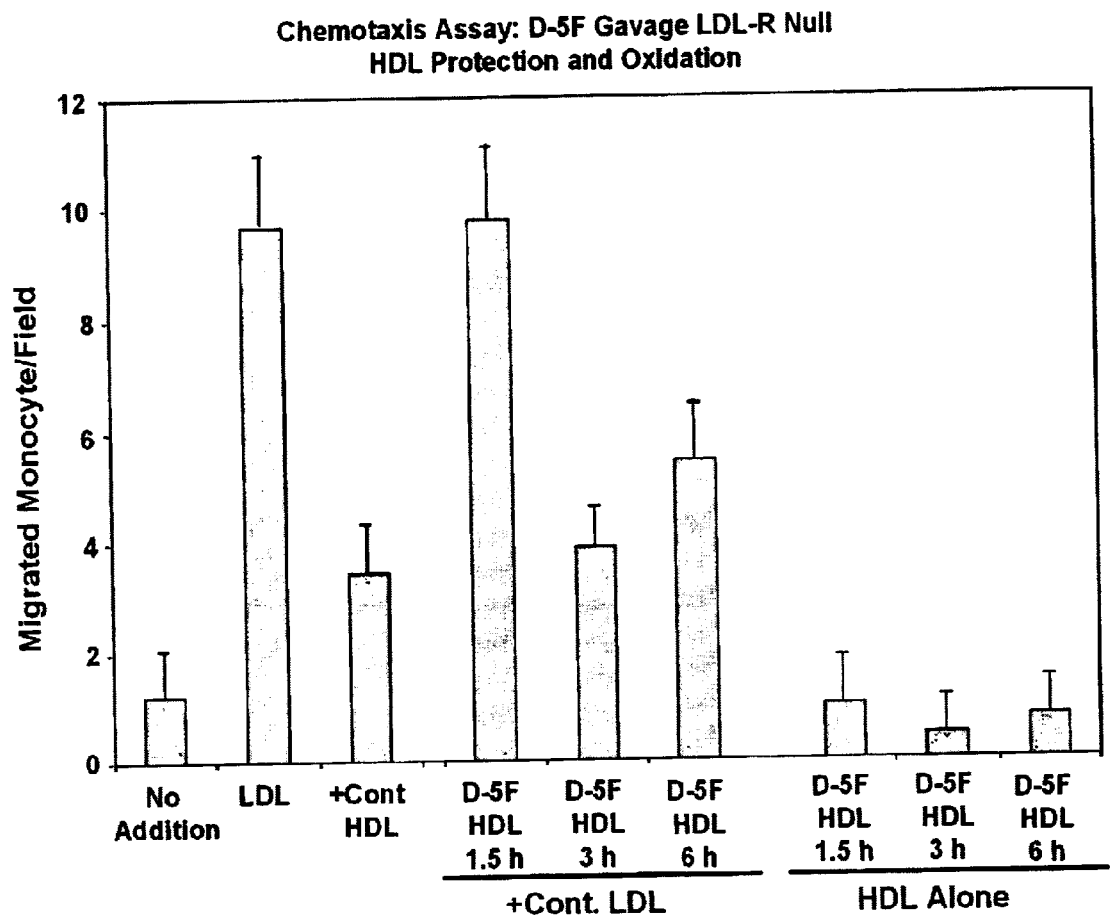
FIG. 8A illustrates the results of a chemotaxis assay comparing control HDL and HDL from mice given the D-peptide by gavage.
Figure 8B:
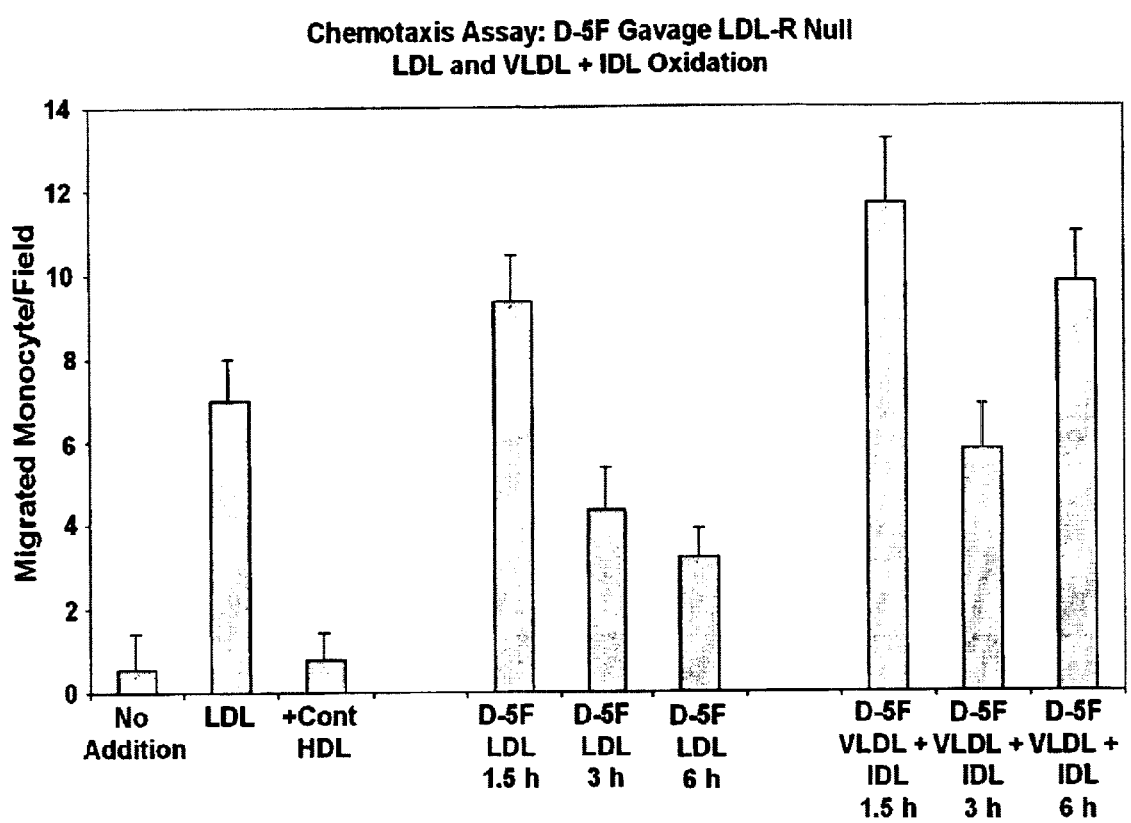
FIG. 8B illustrates the results of a chemotaxis assay comparing LDL and VLDL/IDL from mice given the D-peptide by gavage.

FIG. 8A and FIG. 8B are two graphs from experiments in which LDL receptor knockout mice were given 50 micrograms of D-5F by gavage. The animals were bled 1.5, 3 or 6 hours later and their HDL, LDL, and VLDL/IDL isolated. As indicated in the graph, HDL taken 1.5 hours after gavage did not protect control (cont.) LDL from modification but the HDL taken after 3 hours and slightly less after 6 hours following gavage were as protective against LDL-induced monocyte chemotactic activity production by human artery wall cells as a control HDL (FIG. 8A). In the other graph (FIG. 8B), 1.5, 3, or 6 h after administration of 50 micrograms of D-5F by gavage mouse LDL and VLDL/IDL were isolated. In the left panel a control LDL was added to the human artery wall cells without or with a control HDL and monocyte chemotactic activity produced by the artery wall cells was measured. In the middle panel the mouse LDL taken after 1.5, 3, or 6 hours after gavage of 50 micrograms of D-5F were added to the artery wall cells. The results indicate that after 3 h and 6 h the LDL induced significantly less monocyte chemotactic activity. On the right side of the graph the VLDL/IDL fraction of lipoproteins (V/I LDL) were added and as shown the 3 hour time point induced significantly less monocyte chemotactic activity.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A peptide that ameliorates a symptom of atherosclerosis, wherein:
   said peptide comprises the amino acid sequence of SEQ ID NO:5; and
   said peptide comprises at least one "D" amino acid residue.

2. The peptide of claim 1, wherein said peptide is mixed with a pharmacologically acceptable excipient.

3. The peptide of claim 1, wherein said peptide is mixed with a pharmacologically acceptable excipient suitable for oral administration to a mammal.

4. The peptide of claim 1, wherein all enantiomeric amino acids are "D" amino acids.

5. The peptide of claim 1, wherein said peptide further comprises a protecting group coupled to the amino or carboxyl terminus.

6. The peptide of claim 5; wherein said protecting group is a protecting group selected from the group consisting of acetyl (Ac), amide, 3 to 20 carbon alkyl groups, Fmoc, t-butoxycarbonyl (Tboc), 9-fluoreneacetyl group, 1-fluorenecarboxylic group, 9-fluorenecarboxylic group, 9-fluorenone-1-carboxylic group, benzyloxycarbonyl, Xanthyl (Xan), Trityl (Trt), 4-methyltrityl (Mtt), 4-methoxytrityl (Mmt), 4-methoxy-2,3,6-trimethyl-benzenesulphonyl (Mtr), Mesitylene-2-sulphonyl (Mts), 4,4-dimethoxybenzhydryl (Mbh),Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimethyl-2,6-dioxocyclohexylidene)ethyl (Dde), 2,6-dichlorobenzyl (2,6-DiCl-Bzl), 2-chlorobenzyloxycarbonyl (2-Cl-Z), 2-bromobenzyloxycarbonyl (2-Br-Z), Benzyloxymethyl (Bom), cyclohexyloxy (cHxO),t-butoxymethyl (Bum), t-butoxy (tBuO), t-Butyl (tBu), and Trifluoroacetyl (TFA).

7. The peptide of claim 5; wherein said peptide comprises a protecting group coupled to the amino terminus and said amino terminal protecting group is a protecting group selected from the group consisting of acetyl, propionyl, and a 3 to 20 carbon alkyl.

8. The peptide of claim 1, wherein said peptide comprises a protecting group coupled to the carboxyl terminus and said carboxyl terminal protecting group is an amide.

9. The peptide of claim 5, wherein said peptide comprises a first protecting group coupled to the amino terminus and a second protecting group coupled to the carboxyl terminus.

10. The peptide of claim 9, wherein said peptide comprises:
   a first protecting group coupled to the amino terminus wherein said protecting group is a protecting group selected from the group consisting of acetyl, propionyl, and a 3 to 20 carbon alkyl; and
   a second protecting group coupled to the carboxyl terminus and said carboxyl terminal protecting group is an amide.

11. The peptide of claim 10, wherein all enantiomeric amino acids are "D" amino acids.

12. The peptide of claim 1, wherein more than half of the enantiomeric amino acids comprising said peptide are D amino acids.

13. The peptide of claim 10, wherein said first protecting group is an acetyl and said second protecting group is an amide.

14. A composition suitable for administration to a mammal, that ameliorates a symptom of atherosclerosis, wherein said composition comprises:
   a pharmaceutically acceptable excipient; and
   a peptide comprising the amino acid sequence of SEQ ID NO:5, wherein said peptide comprises at least one "D" amino acid residue, and wherein said peptide has a first protecting group attached to an amino terminal and a second protecting group attached to a carboxyl terminal.

15. The composition of claim 14, wherein said first protecting group and said second protecting group are independently selected from the group consisting of an acetyl (Ac), an amide, a 3 to 20 carbon alkyl group, Fmoc, t-butoxycarbonyl (Tboc), 9-fluoreneacetyl group, 1-fluorenecarboxylic group, 9-fluorenecarboxylic group, 9-fluorenone-1-carboxylic group, benzyloxycarbonyl, Xanthyl (Xan), Trityl (Trt), 4-methyltrityl (Mtt), 4-methoxytrityl (Mmt), 4-methoxy-2,3,6-trimethyl-benzenesulphonyl (Mtr), Mesitylene-2-sulphonyl (Mts), 4,4-dimethoxybenzhydryl (Mbh),Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimethyl-2,6-dioxocyclohexylidene)ethyl (Dde), 2,6-dichlorobenzyl (2,6-DiCl-Bzl), 2-chlorobenzyloxycarbonyl (2-Cl-Z), 2-bromobenzyloxycarbonyl (2-Br-Z), Benzyloxymethyl (Bom), cyclohexyloxy (cHxO),t-butoxymethyl (Bum), t-butoxy (tBuO), t-Butyl (tBu), and Trifluoroacetyl (TFA).

16. The composition of claim 14, wherein said first protecting group is an acetyl.

17. The composition of claim 14, wherein said second protecting group is an amide.

18. The composition of claim 14, wherein more than half of the enantiomeric amino acids comprising said peptide are D amino acids.

19. The composition of claim 14, wherein all enantiomeric amino acids comprising said peptide are D amino acids.

20. The composition of claim 14, wherein said excipient is an excipient suitable for oral administration.

21. The composition of claim 14, wherein said excipient is an excipient suitable for injection.

22. The composition of claim 14, wherein said peptide comprises a plurality of D amino acid residues.

23. A method of ameliorating a symptom of atherosclerosis, said method comprising orally administering to an organism a peptide that:
   comprises the amino acid sequence of SEQ ID NO:5; and
   that comprises at least one "D" amino acid residue.

24. The method of claim 23, wherein said organism is an organism diagnosed as having one or more symptoms of atherosclerosis.

25. The method of claim 23, wherein said organism is an organism diagnosed as at risk for atherosclerosis.

26. The method of claim 23, wherein said organism is a human.

27. The method of claim 23, wherein said organism is a non-human mammal.

28. The method of claim 23, wherein said peptide further comprises a protecting group coupled to the amino or carboxyl terminus of said peptide.

29. The method of claim 28, wherein said protecting group is a protecting group selected from the group consisting of acetyl (Ac), amide, 3 to 20 carbon alkyl groups, Fmoc, t-butoxycarbonyl (Tboc), 9-fluoreneacetyl group, 1-fluorenecarboxylic group, 9-fluorenecarboxylic group, 9-fluorenone-1-carboxylic group, benzyloxycarbonyl, Xanthyl (Xan), Trityl (Trt), 4-methyltrityl (Mtt), 4-methoxytrityl (Mmt), 4-methoxy-2,3,6-trimethyl-benzenesulphonyl (Mtr), Mesitylene-2-sulphonyl (Mts), 4,4-dimethoxybenzhydryl (Mbh),Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimethyl-2,6-dioxocyclohexylidene)ethyl (Dde), 2,6-dichlorobenzyl (2,6-DiCl-Bzl), 2-chlorobenzyloxycarbonyl (2-Cl-Z), 2-bromobenzyloxycarbonyl (2-Br-Z), Benzyloxymethyl (Bom), cyclohexyloxy (cHxO), t-butoxymethyl (Bum), t-butoxy (tBuO), t-Butyl (tBu), and Trifluoroacetyl (TFA).

30. The method of claim 23, wherein said peptide further comprises a first protecting group coupled to the amino terminus wherein said first protecting group is an acetyl and a second protecting group coupled to the carboxyl terminus wherein said second protecting group is an amide.

31. The method of claim 23, wherein said peptide is mixed with a pharmacological excipient.

32. The method of claim 23, wherein said peptide is mixed with a pharmacological excipient suitable for oral administration to a mammal.

33. A method of ameliorating a symptom of atherosclerosis, said method comprising administering to an organism a peptide that
   comprises the amino acid sequence of SEQ ID NO:5; and
   that comprises at least one "D" amino acid residue.

34. The method of claim 33, wherein said peptide further comprises a protecting group coupled to the amino or carboxyl terminus.

35. The method of claim 34, wherein said protecting group is a protecting group selected from the group consisting of acetyl, $CH_3—(CH_2)_n—CO—$ where n ranges from 1 to 20, and an amide.

36. The method of claim 34, wherein said peptide further comprises a first protecting group coupled to the amino terminus and a second protecting group coupled to the carboxyl terminus.

37. The method of claim 36, wherein said first protecting group and said second protecting group are independently selected from the group consisting of an acetyl (Ac), an amide, a 3 to 20 carbon alkyl group, Fmoc, t-butoxycarbonyl (Tboc), 9-fluoreneacetyl group, 1-fluorenecarboxylic group, 9-fluorenecarboxylic group, 9-fluorenone-1-carboxylic group, benzyloxycarbonyl, Xanthyl (Xan), Trityl (Trt), 4-methyltrityl (Mtt), 4-methoxytrityl (Mmt), 4-methoxy-2,3,6-trimethyl-benzenesulphonyl (Mtr), Mesitylene-2-sulphonyl (Mts), 4,4-dimethoxybenzhydryl (Mbh), Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimethyl-2,6-dioxocyclohexylidene)ethyl (Dde), 2,6-dichlorobenzyl (2,6-DiCl-Bzl), 2-chlorobenzyloxycarbonyl (2-Cl-Z), 2-bromobenzyloxycarbonyl (2-Br-Z), Benzyloxymethyl (Bom), cyclohexyloxy (cHxO),t-butoxymethyl (Bum), t-butoxy (tBuO), t-Butyl (tBu), and Trifluoroacetyl (TFA).

38. The method of claim 37, wherein said first protecting group is an acetyl.

39. The method of claim 37, wherein said second protecting group is an amide.

40. The method of claim 37, wherein said first protecting group is an acetyl and said second protecting group is an amide.

41. The method of claim 37, wherein more than half of the enantiomeric amino acids comprising said peptide are D amino acids.

42. The method of claim 37, wherein all enantiomeric amino acids comprising said peptide are D amino acids.

43. The method of claim 40, wherein all enantiomeric amino acids comprising said peptide are D amino acids.

44. A method of ameliorating a symptom of atherosclerosis, said method comprising orally administering to an organism a composition that comprises a peptide that:

comprises the amino acid sequence of SEQ ID NO:5;

that comprises at least one "D" amino acid residue; and wherein said peptide has a first protecting group attached to an amino terminal and a second protecting group attached to a carboxyl terminal.

45. The method of claim 44, wherein said organism is an organism diagnosed as having one or more symptoms of atherosclerosis.

46. The method of claim 44, wherein said organism is an organism diagnosed as at risk for atherosclerosis.

47. The method of claim 44, wherein said organism is a human.

48. The method of claim 44, wherein said organism is a non-human mammal.

49. The method of claim 44, wherein said first protecting group and said second protecting group are independently selected from the group consisting of an acetyl, a $CH_3$—$(CH_2)_n$—CO— where n ranges from 3 to 20, and an amide.

50. The method of claim 44, wherein said first protecting group is an acetyl.

51. The method of claim 44, wherein said second protecting group is an amide.

52. The method of claim 44, wherein said composition further comprises a pharmaceutically acceptable excipient.

53. The method of claim 52, wherein said excipient is an excipient suitable for oral administration.

54. The method of claim 44, wherein said peptide comprises a plurality of D amino acid residues.

55. A kit for ameliorating a symptom of atherosclerosis, said kit comprising a container containing a peptide that comprises the amino acid sequence of SEQ ID NO:5; and that comprises at least one "D" amino acid residue.

56. The kit of claim a 55, wherein said peptide is combined with a pharmaceutically acceptable excipient in a unit dosage formulation.

57. The kit of claim 56, wherein said unit dosage formulation is for oral administration.

58. The kit of claim 55, further comprising instructional materials teaching the use of said peptide for ameliorating one or more symptoms of atherosclerosis.

59. A kit for ameliorating a symptom of atherosclerosis, said kit comprising a container containing a composition suitable for oral administration that ameliorates a symptom of atherosclerosis, wherein said composition comprises a peptide that comprises the amino acid sequence of SEQ ID NO:5;

that peptide comprises at least one "D" amino acid residue; and said peptide has a first protecting group attached to an amino terminal and a second protecting group attached to a carboxyl terminal.

60. The kit of claim 59, wherein said peptide is combined with a pharmaceutically acceptable excipient in a unit dosage formulation.

61. The kit of claim 59, further comprising instructional materials teaching the use of said peptide for ameliorating one or more symptoms of atherosclerosis.

* * * * *